US009976119B2

(12) United States Patent
Lenz et al.

(10) Patent No.: US 9,976,119 B2
(45) Date of Patent: *May 22, 2018

(54) COMPOSITIONS AND METHODS FOR IMPROVING THE QUALITY OF PROCESSED SPERM

(71) Applicant: Inguran, LLC, Navasota, TX (US)

(72) Inventors: Richard Lenz, College Station, TX (US); Juan Moreno, College Station, TX (US); Ramakrishnan Vishwanath, Hamilton (NZ)

(73) Assignee: Inguran, LLC, Navasota, TX (US)

( * ) Notice: Subject to any disclaimer, the term of this patent is extended or adjusted under 35 U.S.C. 154(b) by 72 days.

This patent is subject to a terminal disclaimer.

(21) Appl. No.: 15/157,201

(22) Filed: May 17, 2016

(65) Prior Publication Data
US 2016/0257929 A1    Sep. 8, 2016

Related U.S. Application Data

(63) Continuation of application No. 13/823,843, filed as application No. PCT/US2012/040553 on Jun. 1, 2012, now Pat. No. 9,347,038.

(60) Provisional application No. 61/570,691, filed on Dec. 14, 2011, provisional application No. 61/569,143, filed on Dec. 9, 2011, provisional application No. 61/492,151, filed on Jun. 1, 2011.

(51) Int. Cl.
| *A01N 1/02* | (2006.01) |
| *C12N 5/075* | (2010.01) |
| *C12N 5/076* | (2010.01) |
| *C12N 5/071* | (2010.01) |
| *G01N 15/14* | (2006.01) |

(52) U.S. Cl.
CPC ......... *C12N 5/0609* (2013.01); *A01N 1/0226* (2013.01); *A01N 1/0284* (2013.01); *C12N 5/061* (2013.01); *C12N 5/0612* (2013.01); *C12N 2500/30* (2013.01); *C12N 2500/38* (2013.01); *C12N 2502/04* (2013.01); *G01N 15/1459* (2013.01); *G01N 2015/149* (2013.01)

(58) Field of Classification Search
CPC .... A01N 1/0226; A01N 1/0284; C12N 5/061; C12N 2500/30; C12N 2500/38; C12N 2502/04; C12N 5/0609; C12N 5/0612; G01N 15/1459; G01N 2015/149; G01N 2015/1006
See application file for complete search history.

(56) References Cited

U.S. PATENT DOCUMENTS

| 5,135,759 | A | 8/1992 | Johnson |
| 6,149,867 | A | 11/2000 | Seidel et al. |
| 6,235,783 | B1 | 5/2001 | Surai |
| 6,258,998 | B1 | 7/2001 | Damiani |
| 6,849,394 | B2 | 2/2005 | Rozeboom |
| 7,208,265 | B1 | 4/2007 | Schenk |
| 7,371,517 | B2 | 5/2008 | Evans et al. |
| 7,545,491 | B2 | 6/2009 | Mueth et al. |
| 8,171,430 | B1 | 5/2012 | Kommisrud et al. |
| 8,435,729 | B2 | 5/2013 | Ostermeier |
| 2002/0028849 | A1 | 3/2002 | Godkin |
| 2005/0202394 | A1 | 9/2005 | Dobson |
| 2005/0214733 | A1 | 9/2005 | Graham et al. |
| 2008/0144037 | A1 | 6/2008 | Mueth et al. |
| 2008/0199846 | A1 | 8/2008 | Long |
| 2009/0176271 | A1 | 7/2009 | Durack |
| 2009/0226879 | A1 | 9/2009 | Abdullah |
| 2009/0325878 | A1 | 12/2009 | Dobson |
| 2011/0183415 | A1 | 7/2011 | Chung |
| 2011/0250581 | A1 | 10/2011 | Ostermeier |
| 2013/0183656 | A1 | 7/2013 | Lenz et al. |
| 2013/0295068 | A1 | 11/2013 | Annerl |
| 2013/0337431 | A1 | 12/2013 | Lenz et al. |

FOREIGN PATENT DOCUMENTS

| WO | 2001037655 | 5/2001 |
| WO | 0241906 A2 | 5/2002 |
| WO | 0243486 A1 | 6/2002 |
| WO | 2004087177 | 10/2004 |

(Continued)

OTHER PUBLICATIONS

New Zealand Examination Report dated Jun. 29, 2015 for Appl. No. 617706.
U.S. Office Action dated Sep. 11, 2015 for U.S. Appl. No. 13/844,273.
Varma et al. "Effect of Vitamin E on Human Sperm Motility and Lipid Peroxidation in vitro" Asian J. Androl. (1999) 1(3): 151-154.
Oruch et al. "The fat soluble antioxidant vitamin E: Its metabolism, and biological and physiological significance." Global J. Biochem. (published online Nov. 2010) 2(1): 28-48.
U.S. Office Action dated Sep. 9, 2015 for U.S. Appl. No. 13/823,843.
EP Examination Report dated Sep. 17, 2015 for Appl. No. 12 792 326.6.
AU Examination Report dated Sep. 16, 2015 for Appl. No. 2013202649.
AU Examination Report dated Sep. 16, 2015 for Appl. No. 2012261941.
CO Examination Report dated Aug. 26, 2015 for Appl. No. 13-300556.
AU Notice of Acceptance dated Oct. 9, 2015 for Appl. No. 2012261941.

(Continued)

*Primary Examiner* — Susan M Hanley
(74) *Attorney, Agent, or Firm* — Ryan Christensen; Hashim Rahman

(57) ABSTRACT

The present invention relates to compositions and methods for the handling of processed sperm including samples that are freshly collected, those transported as fresh samples, samples that are frozen and thawed, those sorted into one or more subpopulations, and those that are otherwise processed or handled that impose trauma on the cell. Trauma can reduce the motility, fertility, viability and overall integrity of the sperm and reduce the ability to fertilize, produce an embryo and a healthy offspring. The present invention relates to novel compounds that can be added to the sperm cell sample to reduce the traumatic effects of physical stress during mild as well as extensive sperm cell processing, methods of using the compounds in standard sperm processing procedures, the end products made from these methods including sperm and embryos, as well as methods of using those end products in assisted reproductive biology techniques in animals.

16 Claims, 4 Drawing Sheets

(56) References Cited

FOREIGN PATENT DOCUMENTS

| WO | 2004088283 | | 10/2004 |
|---|---|---|---|
| WO | 2005094852 | | 10/2005 |
| WO | 2005095590 | | 10/2005 |
| WO | 2005095960 | | 10/2005 |
| WO | 200602965 | A1 | 3/2006 |
| WO | 2007087667 | A2 | 8/2007 |
| WO | 2009/086191 | A1 | 7/2009 |

OTHER PUBLICATIONS

AU Examination Report dated Oct. 14, 2015 for Appl. No. 2013202649.
New Zealand Examination Report dated Oct. 1, 2015 for Appl. No. 712027.
New Zealand Notice of Acceptance dated Oct. 1, 2015 for Appl. No. 617706.
Breininger et al. "Alpha-tocopherol improves biochemical and dynamic parameters in cryopreserved boar semen." Therioigenology (2005) 63: 2126-2135.
Definition of alpha-tocopherol downloaded from http://pubchem.ncbi.nlm.nih.gov/compound/alpha-tocopherol on Sep. 2, 2015.
Hollinshead et al. "Birth of lambs of a pre-determined sex after in vitro production of embryos using frozen-thawed sex-sorted and re-frozen-thawed ram spermatozoa." Reproduction (2004) 127: 557-568.
Underwood et al. "In vitro characteristics of frozen-thawed, sex-sorted bull sperm after refreezing or incubation at 15 or 37° C" Theriogenology (2009) 72: 1001-1008).
Foote, R. H. "Fertility of Bull Seman at High Extension Rates in Tris-Buffered Extenders." J Dairy Sci (1970) 53(11), 1475-1477.
U.S. Office action dated Mar. 19, 2015 for U.S. Appl. No. 13/844,273.
U.S. Office action dated Feb. 26, 2015 for U.S. Appl. No. 13/823,843.
Sikka, Suresh "Oxidative Stress and Role of Antioxidants in Normal and Abnormal Sperm Function." Department of Urology, Tulane University School of Medicine, 1996.
Birch et al. "A novel role for vitamin B12: Cobalamins are intracellular antioxidants in vitro" Free Radical Biol. Med. (2009)47: 184-18.
Malo et al. "Anti-oxidant supplementation improves boar sperm characteristics and fertility after cryopreservation: Comparison between cysteine and rosemary (*Rosmarinus officinalis*)" Cryobiology (2010) 61: 142-147.
European Extended Search Report dated Nov. 12, 2014, issued in related EP Application No. 12792326.6 (12 PP).
Anghel, A., et al., "The effects of antioxidants on the cytological parameters of cryopreserved buck semen." Romanian Biotechnological Letters 15.3 (2010): 27.
Lenz R. W., et al., "A comparison of bovine seminal quality assessments using different viewing chambers with a computer-assisted semen analyzer." Journal of animal science 89.2 (2011): 383-388.
Towhidi, A.et al., Combined n-3 Fatty Acids and a-Tocopherol Supplementation Improved the Ovine Sperm Cryosurvival, Iranian Journal of Biotechnology Dec. 2013; 11(4): 238-43.
Restriction Requirement for related U.S. Appl. No. 13/844,843, dated Sep. 30, 2014.
Restriction Requirement for related U.S. Appl. No. 13/844,273, dated Sep. 29, 2014.
Canadian Examination Report for related CA Application No. 2,837,340, dated Oct. 7, 2014.
New Zealand Office Action dated Sep. 25, 2014, issued in related NZ Application 617706 (3 pp).
Australian Office Action dated Jun. 27, 2014, issued in related AU Application No. 2012261941 (5 pp).
Australian Office Action dated Jun. 27, 2014, issued in related AU Application No. 2013202649 (5 pp).
Rath, D., et al., "Improved quality of sex-sorted sperm: A prerequisite for wider commercial application", Theriogenology 71, (2009) 22-29.
Klinc, P., et al., Improvement of sperm sorting eficiency and fertilizing capacity employing two variations of a new bull semen extender (Sexces®) (Abstract 1 p).
Camara, D.R., et al., "Effects of antioxidants and duration of pre-freezing equilibration on frozen=thawed ram semen." Theriogenology, vol. 76, Issue 2,Jul. 15, 2011, pp. 342-350 (Abstract 1 pp).
Satpute, RM, et al., "Effect of alpha-ketoglutarate and N-acetyl cysteine on cyanide-induced oxidative stress mediated cell death in PC12 cells", Toxicol Ind Health Jun. 2010 vol. 26 No. 5 297-308.
De Graaf, SP, et al., "The influence of antioxidant, cholesterol and seminal plasma on the in vitro quality of sorted and non-sorted ram spermatozoa", vol. 67, Issue 2,Jan. 15, 2007, pp. 217-227 (Abstract 1 pp).
Vallorani, C., et al., "Effects of antioxidants on boar spermatozoa during sorting and storage", vol. 122, Issues 1-2, Oct. 2010, pp. 58-65 (Abstract 1 pp).
Gadea, J., et al., "Supplementation of the Thawing Media With Reduced Glutathione Improves Function and the In Vitro Fertilizing Ability of Boar Spermatozoa After Cryopreservation", Journal of Andrology, vol. 26, No. 6, pp. 749-756, Nov./Dec. 2005 (Abstract p. 1).
"Tocopherol", Wikipedia, 2012, Web. May 30, 2012, http://en.wikipedia.org/wiki/Tocopherol, pp. 1 and 2 (2 pages).
"Vitamin", Wikipedia, 2012, Web. May 30, 2012, http://en.wikipedia.org/wiki/Vitamin, (1 page).
U.S. Office action dated Mar. 19, 2015 for U.S. Appl. No. 13/844,636.
U.S. Office action dated Sep. 16, 2015 for U.S. Appl. No. 13/844,636.
U.S. Notice of Allowance dated Mar. 24, 2016 issued in related U.S. Appl. No. 13/844,636.
U.S. Notice of Allowance dated Mar. 3, 2016 issued in related U.S. Appl. No. 13/844,273.
U.S. Notice of Allowance dated Mar. 1, 2016 issued in related U.S. Appl. No. 13/823,843.
CA Examination Report dated Jan. 22, 2016 in related CA Application No. 2,837,340.
"Cobalt in food," Cobal Development Institute, Web. Feb. 2006, http://www.thecdi.com/cdi/images/documents/Cobalt_food_Feb_06.pdf (4 pages).
"The Effects of Cobalt Exposure on the mammalian Reproductive System," Cobalt Development Institute, Web. Nov. 2006, http://www.thecdi.com/cdi/images/documents/reprotox%20final.pdf, (2 pages).
"Vitamin B-12." Encyclopeadia Britannica. Encyclopaedia Britannica Online. Encyclopaedia Britannica Inc., 2012. Web. May 28, 2012, http://www.britannica.com/Ebchecked/topic/631051/vitamin-B12, (3 pages).
"Vitamin B-12 (cobalamin)," University of Maryland Medical Center Website, Page URL: http://www.umm.edu/altmed/articles/vitamin-b12-000332.htm, obtained May 14, 2012 pp. 1-4 (4 pages).
"Vitamin B12 Deficiency," Wikipedia, 2012, Web. May 28, 2012, http://en.wikipedia.org/wiki/Vitamin_B12_deficiency, pp. 1,2, and 10 (3 pages).
Abd-Elmoaty et al., "Increased levels of oxidants and reduced antioxidants in semen of infertile men with varicocele," Fertility and Sterility, American Society for Reproductive Medicine, vol. 94, No. 4, Sep. 2010 pp. 1531-1534 (4 pages).
Bansal, A.K., Bilaspuri, G.S., "Impacts of Oxidative Stress and Antioxidants on Semen Functions," SAGE-Hindawi Access to Research, Veterinary Medicine International, vol. 2011, Article ID 686137, (7 pages).
Baumber et al., "The Effect of Reactive Oxygen Species on Equine Sperm Motility, Viability, Acrosomal Integrity, Mitochondrial Membrane Potential, and Membrane Lipid Peroxidation," Journal of Andrology, vol. 21, No. 6, Nov./Dec. 2000 pp. 895-902. (1 page).

(56) References Cited

OTHER PUBLICATIONS

Bencic et al., "Carbon Dioxide Reversibly Inhibis Sperm Motility and Fertilizing Ability in Steelhead (*Oncorhynchus mykiss*)," 2000, Fish Physiology and Biochemistry, vol. 23(4), pp. 275-281 (7 pages).
Best, et al., "Nuclear Localization of Pyrrole-Imidazole Polyamide-Flourescein Conjugates in Cell Culture," PNAS, 2003, vol. 100(21), pp. 12063-12068. (6 pages).
Bilodeau et al., "Thiols Prevent H2O2-Mediated Loss of Sperm Motility in Cryopreserved Bull Semen," Theriogenology, vol. 56, Issue 2, Jul. 15, 2001, pp. 275-286 (12 pages) vbTab.
Blanusa et al., "Chelators as Antidotes of Metal Toxicity: Therapeautic and Experimental Aspects," Current Medicinal Chemistry, Bentham Science Publishers Ltd, 2005, 12, 2771-2794. (25 pages).
Boatman et al., "Bicarbonate Carbon Dioxide Regulation of Sperm Capacitation Hyperactivated Motiliy and Acrosome Reations," 1991, Biol of Reprod, vol. 44(5), pp. 806-813. (8 pages).
Bruemmer, et al., "Effect of Pyruvate on the Function of Stallion Spermatozoa Stored for up to 48 Hours," J Anim Sci, 2002, vol. 80, pp. 12-18 (8 pages).
Bucher, John R., "Toxicity Studies of Cobalt Sulfate Heptahdrate," U.S. Department of Health and Human Services, National Toxicology Program, NIH Pub. No. 91-3124, Research Triangle Park, North Carolina, Jan. 1999, 6-11 ( 11 pages)vbTab.
Cai et al., "The effect of adding vitamin B12 in sperm diluter on quality of bull\s straw frozen sperm," J Liaoning Anricultural Collene, 2004, 6, 10-11. (Abstract) (1 page).
Chen et al., "Comparison of seminal vitamin B12, folate, reactive oxygen species and various sperm parameters between fertile and infertile males," Department of Clinical Nutrition, School of Public Health, Sun Yat-sen University of Medical Sciences, China, 2001 (Abstract) (1 page).
Denniston, et al., "Effect of Antioxidants on the Motility and Viability of Cooled Stallion Spermatozoa," J Reprod of Fertil, 2001, Supplement 56, pp. 121-126 (Abstract) (1 page).
Dike, I.P., "Efficiency of intracellular cryoprotectants on the cryopreservation of sheep oocytes by controlled slow freezing and vitrification techniques," Journal of Cell and Animal Biology, vol. 3, Mar. 2009, pp. 044-049 (6 pages).
Farrell, et al., "Quantification of Bull Sperm Characteristics Measured by Computer-Assisted Sperm Analysis (CASA) and the Relationship to Fertility," Theriogenology, 1998, vol. 49, pp. 871-879. (10 pages).
Garcia, et al., "Development of a Buffer System for Dialysis of Bovine Spermatozoa Berfore Freezing III. Effect of Different Inorganic and Organic Salts on Fresh and Frozen-Thawed Semen," 1989, Theriogenology, vol. 31(5), pp. 1039-1048 (10 pages).
Graves, et al., "Metabolic End-products of Anaerobic Spermaozoan Metablism," 1966, Nature, vol. 211, pp. 308-309. (2 pages).
Graves, et al., "Metabolism of Pyruvate by Epididymal-Like Bovine Spermatozoa," 1964, J Dairy Sci, vol. 47(12), pp. 1407-1411vbTab (6 pages).
Griveau et al., "Reactive oxygen species, lipid peroxidation and enzmatic defense systems in human spermatozoa," Journal of Reproduction and Fertility, 1995, 103, 17-26 (10 pages).
Guthrie et al., "Flow Cytometric Sperm Sorting: Effects of Varying Laser Power on Embryo Developmen in Swine," 2002, Moecular Reproduction and Development, vol. 61, pp. 87-92 (6 pages).
Ha et al. "Vitamin B complex as a complements in the cryopreservation dilutions of the ram semen," Journal of Gansu Agricultural University, 2003, 38, 17-19, (Abstract) (1 page).
Ha et al. "Vitamin B complex as a Complements in the Thawing Dilutions of the Ram Semen," China Herbivores, 2003, 23, 19-20, (Abstract) (1 page).
Hu, J-H, "Effects of Addition of Vitamin B12 to the Extender on Post-Thaw Motility, Acrosome Morphology, and Plasma Membrane Integrity in Bull Semen" Turk. J. Vet. Anim. Sci (209) 33(5): 379-84 (6 pages).

Hu, J-H, "The Cryoprotective Effects of Vitamin B12 Supplementation on Bovine Semen Quality" Reprod Dom Anim, 2011, 46: 66-73 (8 pages).
Johnson, et al., "Flow Cytometry of X and Y Chromosome-Bearin Sperm for DNA Using an Improved Preparation Method and Staining with Hoechst 33342," Gamete Research, 1987, vol. 17, pp. 203-212 (10 pages).
Johnson, L.A., "Sex Preselection by Flow Cytometric Separation of X and Y Chromosome-Bearing Sperm Based on DNA Difference: A Review," 1995, Reprod. Fert. Dev., vol. 7, pp. 893-903.vbTab(11 pages).
Johnson, L.A., "Sex Preselection: High-Speed Fow Cytometric Sorting of X and Y Sperm for Maximum Efficiency," 1999, Theriogenology, vol. 52 (8), pp. 1323-1341. (11 pages).
Juanchi, X., Radiolysis of Cyanocobalamin (vitamin B-12). Radiat. Phys. Chem. 57, 337-339. (3 pages).
Kaeoket, Kampon, "Cryopreservation of Boar Spermatozoa: An Important Role of Antioxidants," Current Frontiers in Cryopreservation, InTech, Chapter 7, Mar. 2012, http://www.intechopen.com/books/current-frontiers-in-cryopreservation/cryopreservation-of-companion-andlivestock-animal-spermatozoa-an-important-role-of-antioxidants, pp. 139-164 (26 pages).
Klinc, P., Rath., "Reduction of Oxidative Stress in Bovine Spermatozoa During Flow Cytometric Sorting," Reproduction in Domestic Animals, vol. 42, Issue 1, Jan. 3, 2007, (pp. 63-67).
Klinc—Dissertation: "Improved Fertility of Flowcytometrically Sex Selected Bull Spermatozoa" Aus dem Institut für Tierzucht Mariensee, 2005 (108 pages).
Lenz, R.W., Kjelland, M.E., VonderHaar, K., Swannack, T.M., and Moreno, J.F., "A comparison of bovine seminal quality assessments using different viewing chambers with a computer-assisted semen analyzer," Journal of Animal Science, American Society of Animal Science, 2011, vol. 89, pp. 383-388 (6 pages).
Li, Shi-Feng et al., "The Protective effects of alpha-ketoacids against oxidative stress on rat spermatozoa in vitro" Asian Journal of Andrology, 2010, vol. 12, (pp. 247-256) (10 pages).
Lodge et al., "Carbon Dioxide in Anaerobic Spermatozoan Metabolism," 1968, vol. 51 (a), pp. 96-103 (8 pages).
Miller, N.A. Fike, K., Grieger, D., Castro, A., Dean, D., "Effect of Melenestrol Acetate and Groth Promotants on Oocyte Yield, Quality, Fertilization Rate and Developmental Competence of In Vitro Embryo Production in Beef Heifers", Kansas State University, Manhattan, KS, Oct. 20, 2011. (Abstract) (1 page).
Ogbuewu et al., "Spermatozoa Manipulation Techniques: A Current Assisted Reproduction Technology Tool Kit in Reproductive Physiology," Journal of Medical Science, Jul. 1, 2010, 10 (5), (pp. 110-123).
Salisbury, G. W. and VanDemark, N. L. "Physiology of Reproduction and Artificial Insemination of Cattle." San Francisco: Freeman and Company. p. 442-551 (1978) ( 1961 & 1978 Combined) Chapters 16 and 17 are the complete article.
Resende, Max V., Bezerra, Marcelo B., Lucio, Aline C., and De Lima, Vera., "Separation of X-Bearing Bovine Sperm by Centrifugation in Continuous Percoll and Optiprep Density Gradient: Effect in Sperm Viability and In Vitro Embryo Production," Ciencia Animal Brasileira, V. 10, N.2, abr./Jun. 2009, p. 581-587.
Salamon, S., Maxwell, W.M.C., "Frozen storage of ram semen I. Processing, freezing, thawing and fertility after cervical insemination," Animal Reproduction Science, 37, 1995, 185-249. (65 pages).
Salisbury, G.W., Reversal by Metabolic Regulators of CO2-induced Inhibition of Mammalian Spermatozoa, 1959, Proc Soc Exp Biol Med, vol. 101(1), pp. 197-189 (4 pages).
Schenk, et al., "Cryopreservation of Flow-Sorted Bovine Spermatozoa," Theriogenology, 1999, 52, pp. 1375-1391 (17 pages).
Stryer, L., "Biochemistry" second edition, 1981, WH Freeman, San Fransico, p. 419-21 (5 pages).
Upreti et al., "Studies on Aromatic Amino Acid Oxidase Activity in Ram Spermatozoa: Role of Pyruvate as an Antioxidant," Anim Reprod Sci, May 29, 1998, 51(4), pp. 275-287 (13 pages).
Watanabe et al. "The effects of dietary vitamin B12 deficiency on sperm maturation in developing and growing male rats," Congential Anomalies, 2003, 43, 57-64 (8 pages).

(56) References Cited

OTHER PUBLICATIONS

Watson, P.F., "The causes of reduced fertility with cryopreserved semen," Animal Reproduction Science, 60-61, 2000, pp. 481-492 (12 pages).
White, I.G. "Studies of the Spermicidal Activity of Chelating Agents." Australian Journal of Biological Sciences 8, 1955, pp. 387-395 (9 pages).
International Search Report dated Oct. 2, 2012 issued in corresponding PCT Application No. PCT/US2012/40553 filed on Jun. 1, 2012.
U.S. Appl. No. 61/492,151, filed Jun. 1, 2011vbTabvbTabvbTabvbTabvbTabvbTab.
U.S. Appl. No. 61/569,143, filed Dec. 9, 2011vbTabvbTabvbTabvbTabvbTabvbTab.
U.S. Appl. No. 61/570,691, filed Dec. 14, 2011vbTab.
U.S. Appl. No. 13/823,843, filed Mar. 15, 2013.
U.S. Appl. No. 13/844,273, filed Mar. 15, 2013.
Klinc, P. "Insemination with Sex Sorted Fresh Bovine Spermatozoa Processed in the Presence of Antioxidative Substances." Reprod Dom Anim 42, 58-62 (2007).
New Zealand Further Examination Report dated Jul. 19, 2016 issued in related NZ Appl. No. 712027.
EP Decision to Refuse dated Aug. 28, 2016 issued in EP Appl. 12792326.6.
New Zealand Further Examination Report dated Feb. 14, 2017 issued in related NZ Appl. No. 725104.
Canadian Examination Report dated Jan. 18, 2017 issued in related CA Appl. No. 2,837,340.
U.S. Office Action dated Feb. 9, 2017 issued in related U.S. Appl. No. 14/997,933.
New Zealand Further Examination Report dated Apr. 28, 2017 issued in related NZ Appl. No. 725104.
New Zealand Further Examination Report dated May 5, 2017 issued in related NZ Appl. No. 731211.
U.S. Notice of Allowance dated May 18, 2017 issued in related U.S. Appl. No. 14/997,933.
New Zealand Further Examination Report dated Oct. 27, 2016 issued in related NZ Appl. No. 725104.
Australian Examination Report dated Nov. 23, 2016 issued in related NZ Appl. No. 2016200319.
Argentinian Examination Report dated Aug. 26, 2017 issued in related AR Appl. No. 20120104505.
Australian Notice of Acceptance dated Oct. 11, 2017 issued in related AU Appl. No. 2016200319.
Canadian Requisition by the Examiner dated Jan. 11, 2018 issued in related CA Appl. No. 2,837,340.

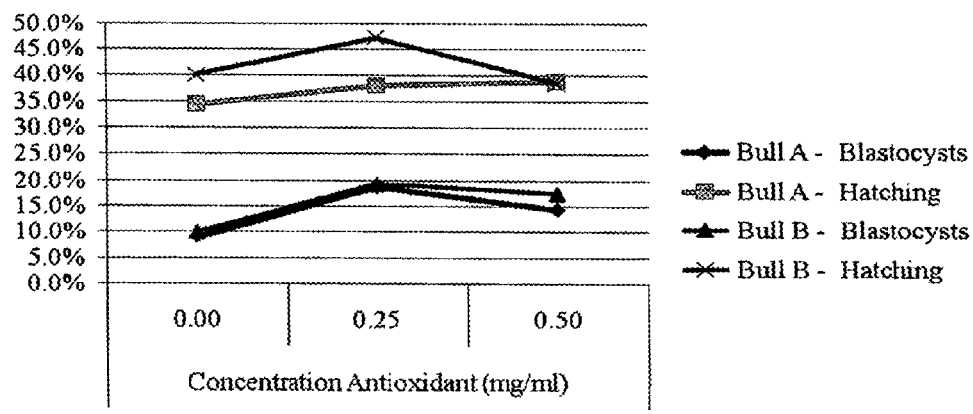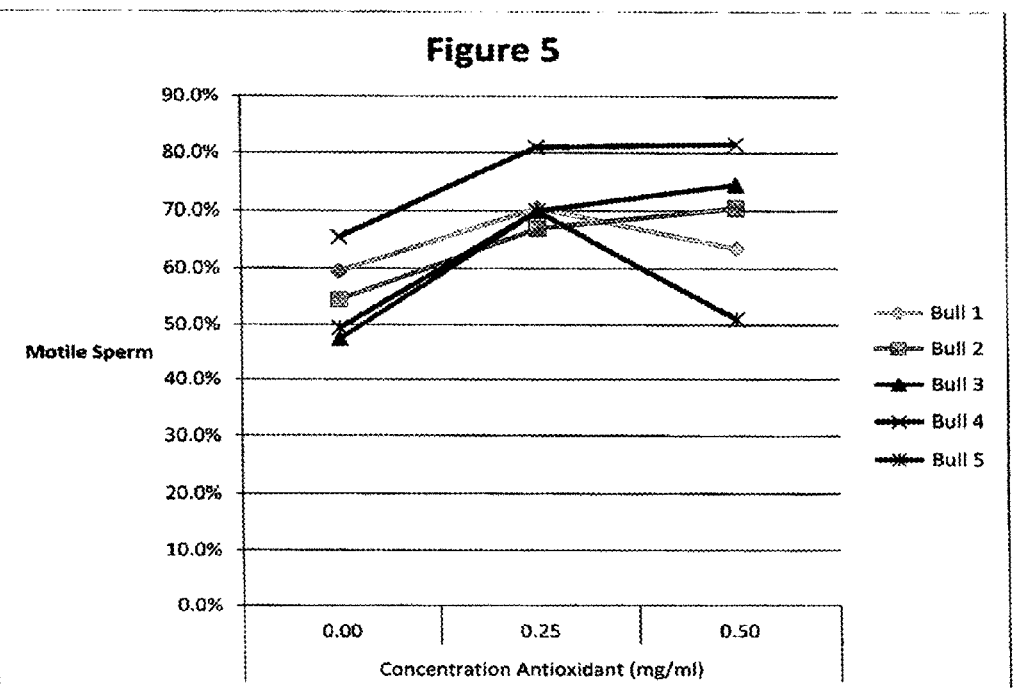

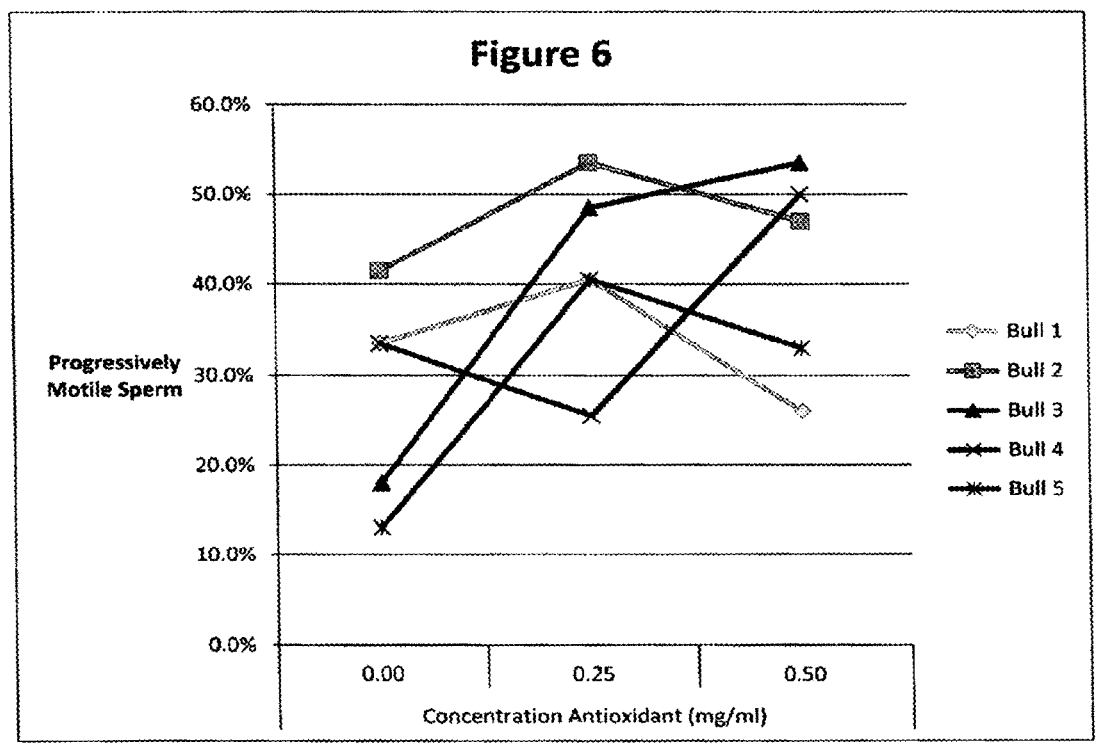

COMPOSITIONS AND METHODS FOR IMPROVING THE QUALITY OF PROCESSED SPERM

This application is a Continuation of the U.S. National Stage application Ser. No. 13/823,843 filed Mar. 15, 2013, now U.S. Pat. No. 9,347,038, of International Application No. PCT/US2012/040553, filed Jun. 1, 2012, which claims priority to U.S. Provisional Applications 61/492,151 filed Jun. 1, 2011, 61/569,143 filed Dec. 9, 2011, and 61/570,691 filed Dec. 14, 2011, the contents of which are all incorporated by reference in their entireties.

The present invention generally relates to compositions and methods for the handling of processed sperm populations, including those freshly collected as well as those sorted into one or more subpopulations, and for treating processed and/or handled semen samples and solutions that contain sperm cells to increase the overall quality of the processed sperm, including their viability, motility, fertility, DNA integrity, and in vitro longevity. The present invention also relates to compositions comprising sperm cells and at least one compound that may be an antioxidant, vitamin or other organic stress reducer, the methods of using these compounds to reduce trauma and stress on processed sperm, the resulting sperm and embryo end products, and the methods of use of these products in assisted reproductive technologies (ART) to increase the quality, quantity and viability of embryos, and improved rates of births in animals.

BACKGROUND

Assisted reproductive technology (ART) includes such techniques as in vitro fertilization (IVF), artificial insemination (AI), intracytoplasmic sperm injection (ICSI) (other techniques using enucleated cells) and multiple ovulation and embryo transfer (MOET) (as well as other embryo transfer techniques), is used across the animal kingdom, including humans and other animals. ART methods are usually expensive, time consuming and marginally successful given the inherent fragility of gametes and embryos when outside of their natural environments. Furthermore, the use of ART within the animal breeding industry in a commercially feasible manner is additionally challenging due to the limited availability of genetically desirable gametes and zygotes. One way to lower the cost of ART and to improve its commercial feasibility is to increase the efficiency of the involved processes by improving the viability and overall quality of gametes and zygotes. Although there is has been a growing interest in this field over the course of the last decade or so, there still remains a strong need to increase the overall quality of gametes and zygotes for use in ART, especially when breeding focuses on pre-natal gender selection, including improving their viability (in the case of gametes and zygotes), their motility and fertility (in the case of sperm cells), as well as other longevity characteristics.

For example, in conventional AI, one problem limiting its commercial application in certain species is the need to use extremely high number of sperm cells per AI dose to ensure successful fertilization. Similarly, in IVF, the percentage of zygotes that develop into embryos remains frustratingly low; this high rate of loss significantly increases the cost of embryos and related services to end-users. There also remains the need for more efficient and lower cost procedures for improving post-embryo handling through cryopreservation as well as non-frozen transport. Cryopreservation of embryos is limited by the success rate of embryo production as well as blastocyst growth in vitro. Currently, only a marginal percentage of IVF embryos are suitable for cryopreservation which adds to the ongoing high cost of ART procedures.

Especially when processing gametes such as flushed oocytes or sperm cells, both conventional and sex-sorted, before their use in ART adds a tremendous amount of stress on the gamete cell and negatively impacts their cellular integrity and membrane structure which in turn is reflected in decreased viability, motility and fertility. An example of processing gametes prior to their use in ART is the sorting of sperm cells based on sex (known as "gender enrichment" or "sex-sorting"), which is a highly desired procedure to minimize wasted births of the wrong sex for selective breeding in the livestock industry but is often cost prohibitive and can be risky to those with smaller breeding herds.

The popular flow cytometry based sex-sorting process severely stresses and damages the cells and produces a low percentage of useful sperm, which although capable of fertilizing matured oocytes, have reduced viability, motility and fertility after the sex-sorting process. Typically, sex-sorting involves many harsh steps including but not limited to: the initial collection and handling of sperm ejaculate which naturally starts to deteriorate rapidly upon collection; the staining of sperm cells which involves binding of an excitable dye to the DNA or a harmful membrane selection procedure; the physical sorting of the sperm cells using high energy fluorescence that physically energizes the dye that is bound to the DNA, forced orientation through a narrow orifice, and application of an electrical charge to the cell; the physical collection of the cells into a container which often shocks the fragile cell upon contact; the osmotic stresses associated with dilution of the sperm droplet in collection media; and the storage of the sorted sperm usually by freezing which is well known to raise havoc with the cell's membrane systems. Each step places the processed sperm under abnormal stress which diminishes the overall motility, viability and/or fertility of the sperm. The result can lead to less efficient samples for use in ART, such as IVF and AI, and other types of subsequent or further processing.

Even non-sorted processed sperm exhibits significant losses in fertility, viability and motility when being collected, handled and transported without freezing, and noticeably experiences significant stress when mixed with cryoprotectant and is frozen and thawed. Many in the field have tried to improve methods for the use on unsorted, conventional semen to minimize loss in the handling processes associated with in vitro handling, preservation and use of semen samples.

Regardless of the processing, sperm lose their potential to fertilize when exposed to: elevated temperatures, abnormal buffers, stains, altered pH systems, physical pressurized orientation as when forced through a nozzle or when oscillated to form drops in a flow cytometer, radiation used to illuminate the DNA binding dye, physical stressors associated with separation and collection techniques, cryoprotectants, freezing, thawing and micromanipulation by the handler.

The large class of compounds referred to as antioxidants have been associated with providing beneficial effects to all sorts of cells, in vivo and in vitro, but these effects are as varied as the nature of the antioxidant itself. An antioxidant is simply one of a large variety of molecules that either inhibit the oxidation of another molecule, becomes oxidized itself in place of the target substrate, or binds harmful free radical intermediates and interrupts oxidative chain reactions within a cell. Most have dual roles; some are enzymes, others are non-enzymatic; some others are vitamins and others are cofactors. Such diversity lauds the diversity of antioxidants, but because of their known ability to minimize cell damage, they are frequently lumped together as a single class of compounds having only a single function, to bind free radicals.

Various antioxidants have shown promise in promoting cell integrity with some reports showing positive effects on sperm motility and membrane integrity during cryopreservation, but some tests have been shown to have minimal or even harmful effects on processed sperm.

Similarly, vitamins are again a rather diverse group of molecules having very different biological properties. Vitamins are any of a large group of organic compounds required in very small amounts as vital nutrients for an organism that cannot synthesize it. They can be antioxidants, enzymes, hormones or non-enzymes; they can be regulators of cell growth, cell differentiation or moderators of mineral metabolism.

To date, no studies have sufficiently addressed the use of antioxidants, vitamins or other supplements in the routine handling of fragile gametes during in vitro processing, especially during the harsh processing associated with the sex-sorting of sperm, whereby the end result is a reproducible improvement on the viability, motility and fertility of extensively processed sperm cells and embryos. There remains a continuing need to improve current methods of ART to reduce the cost and to make the procedures more dependable and commercially feasible to those on a tight budget, especially those smaller breeders who view sex-selection breeding as a high risk and expensive option.

SUMMARY OF THE INVENTION

A broad object of the present invention is to provide improvements in the motility, viability, fertility and overall integrity of processed sperm cells. Accordingly, one embodiment of the present invention comprises a method of treating sperm cells by adding at least one "organic stress reducing" agent (OSR) which may comprise an antioxidant, a vitamin or other organic molecule involved directly or indirectly in modulating physiological stresses in the cell. The OSR would be added in the concentration range of 0.01 mg/ml to 5 mg/ml to a sperm cell sample to form a sperm cell composition. In certain embodiments, one or more OSRs, each in the concentration range of 0.01 mg/ml to 5 mg/ml, can be added to the sperm cell sample prior to cryopreservation (including, for example, freezing and vitrification), after the sperm cell sample has been thawed, or at both times. In other embodiments, the OSR can be added at one or more of the various stages during the sperm cell processing procedure. The term "sperm cell sample" may comprise a processed semen sample or an unsorted, conventional semen sample.

Another specific embodiment of the invention comprises the sperm cell composition comprising a sperm cell sample and at least one OSR in the concentration range of 0.01 mg/ml to 5 mg/ml. Another embodiment encompasses a "sperm cell composition" comprising a sperm cell sample, at least one OSR in the concentration range of 0.01 mg/ml to 5 mg/ml and a cryoprotectant. Most cryoprotectants can be used with the invention, including but not limited to egg yolk, propylene glycol, dimethyl sulfoxide, sucrose, ethylene glycol and glycerol, or a combination thereof. One embodiment encompasses a fresh, an unfrozen, a frozen, a vitrified, or a thawed sperm cell composition comprising a sperm cell sample and at least one OSR in the concentration range of 0.01 mg/ml to 5 mg/ml. Another embodiment encompasses a fresh, an unfrozen, a frozen, a vitrified, or a thawed sperm cell composition comprising a sperm cell sample, at least one antioxidant and/or one vitamin in the concentration range of 0.01 mg/ml to 5 mg/ml, and a stain.

Another broad object of the present invention is to improve the motility, viability (including longevity and ability to survive environmental stress) and/or fertility of sperm cells, each contributing to the sperm cell's overall integrity, to improve the success of using ART, including techniques such as IVF, AI, ICSI (as well as other techniques using enucleated cells), and MOET (as well as other embryo transfer techniques).

Such ART techniques involve different levels of gamete cell processing which in the case of sperm can entail, by example only and is not limited to one or more of the following: artificially collecting a semen sample from the male animal which may involve natural, electronic or other types of sexual stimulation; holding; transporting; buffering with different pHs; chilling; warming; staining; diluting; concentrating; energetically exciting as with a laser; electronic charging; deflecting; ablating to kill unwanted cells usually with targeted lasers; sorting; collecting; shaking; oscillating; magnetically separating; oxygenating as associated with microchip sorting procedures; labeling; precipitating; centrifuging; resuspending; mixing; dialyzing; cryostabilizing; freezing; vitrification; thawing; culturing; inseminating; microinjecting; microfluidic processing; microchip processing; jet and air processing; flow cytometry processing; and similar handling techniques. Whereas a single processing step may exert only minimal stress on a sperm cell, others or a combination may add significant stress, often killing the cell. An extreme example is the sex-sorting process used to separate X- from Y-chromosome bearing cells; the sorting process combines a large number of independent highly stressful steps that severely compromise the overall integrity of the sorted sperm cell population.

Accordingly, one embodiment of the present invention resides broadly in the use of a sperm cell composition, comprising a sperm cell sample and at least one antioxidant and/or at least one vitamin in the concentration range of 0.01 mg/ml to 5 mg/ml, in ART. One specific embodiment of the invention comprises a method of increasing the percentage of zygotes that develop into embryos in a given sample in a given amount of time, as well as increasing the percentage of embryos that are suitable for cryopreservation (i.e., the percentage of embryos that are blastocysts, expanded and hatching blastocysts, or hatched blastocysts), by mixing an egg with a sperm cell sample that has been treated with at least one OSR in the concentration range of 0.01 mg/ml to 5 mg/ml. A further embodiment of the invention resides in a method of making an embryo comprising mixing at least one egg with a sample of sperm cells treated with at least one OSR in the concentration range of 0.01 mg/ml to 5 mg/ml. The embryos produced by this method constitute a further embodiment of the invention. Another embodiment includes a method for inseminating an organism through an AI technique using a sperm cell sample treated with at least one OSR in the concentration of 0.01 mg/ml to 5 mg/ml. Another embodiment includes a method of transferring an embryo into a receptive female (ET) where said embryo is made using a sperm cell sample treated with at least one OSR in the concentration of 0.01 mg/ml to 5 mg/ml. The progeny of the organism that results from the aforementioned AI method also constitutes an embodiment of the invention.

Most embodiments of the invention utilize concentrations of OSRs selected from the following ranges: 0.01 to 5.0 mg/ml; 0.01 to 0.25 mg/ml; 0.01 to 0.5 mg/ml; 0.01 to 1 mg/ml; 0.01 to 2.5 mg/ml; 0.01 to 5 mg/ml; 0.05 to 0.1 mg/ml; 0.05 to 1.0 mg/ml; 0.05 to 2.5 mg/ml; 0.1 to 0.25 mg/ml; 0.1 to 0.5 mg/ml; 0.1 to 1 mg/ml; 0.1 to 2.5 mg/ml; 0.1 to 5 mg/ml; 0.15 to 0.45 mg/ml; 0.15 to 0.5 mg/ml; 0.25 to 0.35 mg/ml; 0.25 to 0.5 mg/ml; 0.25 to 1 mg/ml; 0.25 to 2.5 mg/ml; 0.25 to 5 mg/ml; 0.35 to 0.5 mg/ml; 0.35 to 1 mg/ml; 0.35 to 2.5 mg/ml; 0.35 to 5 mg/ml; 0.5 to 1 mg/ml; 0.5 to 2.5 mg/ml; 0.5 to 5 mg/ml; 1 to 2.5 mg/ml; 1 to 5 mg/ml; about 0.05 mg/ml; about 0.1 mg/ml; about 0.15 mg/ml; about 0.25 mg/ml; about 0.35 mg/ml; about 0.45 mg/ml; and about 0.5 mg/ml.

In some embodiments of the invention the sperm cell composition can be used immediately or processed within the first few minutes after addition of the OSR for whatever processing step is needed, whereby the holding period would be in the range 2 sec to 3 min. In other embodiments, the sperm cell composition is held after the addition of the OSR(s) to allow the OSR(s) to incorporate into the cells and effectuate protective effects on the cell population. Such holding periods can be short, as in the range of a 3-15 minutes, moderate as in the range of 15 min to 1 hr; and longer processing periods ranging up to about 8 hrs or overnight for extensive processing such as with sex-sorting techniques. Transportation hold periods associated with transporting unfrozen sperm cell compositions can be much longer, extending up to a few days, which may for example occur if the sample is collected, treated with the addition of one or more OSRs, transported or shipped to another location possibly by air, and further processed at the second location as for sex-sorting at a designated facility. In other instances, the sperm cell composition might need to be held for a few days while a recipient female is hormonally prepped for artificial insemination, as might occur if a sample is mistakenly thawed and cannot be refrozen. The addition of OSRs could theoretically prolong these extended hold periods over what is currently accepted in the art, and could provide sufficient protection to the sperm in the sperm cell composition so that they could remain viable and fertile for up to a week or more.

In some embodiments of the invention, the OSR is added several times during a complex processing procedure to minimize cell stress throughout the procedure. In other embodiments, the OSR is added only at one or more particular steps which are notably harsh on the cells to help minimize stress and fatigue on the sperm cells. By way of example, the staining process during sex sorting is often performed at non-physiological pH and at elevated temperatures, both known to be harsh on the cells. Similarly, cryopreservation is also extremely harsh on the cells and disrupts cell membranes, both internal and external. Following an intensive multi-step sorting procedure, sex-sorted sperm cells which are already compromised are even more susceptible to cryogenic and freeze processing.

Various OSRs can be used in the context of the current invention, including but not limited to: catalase, superoxide dismutase (SOD), SOD mimics, glutathione, glutathione reductase, glutathione peroxidase, pyruvate, mercaptoethanol, butylated hydroxytoluene (BHT), lipoic acid, flavins, quinines, vitamin K (and related vitamers), vitamin B12 (and related vitamers), with 'vitamers' defined as compounds having the same vitamin activity (such as cobalamin, cyanocobalamin, methylcobalamin, adenosylcobalamin, hydroxocobalamin, and pseudo-B12), vitamin E (including its vitamers, tocopherols ($\alpha$, $\beta$, $\gamma$), tocotrienols, and $\alpha$-tocopheryl), alpha-ketoglutarate (also known as $\alpha$-KG, AKG or oxo-glutarate) and various biological forms of AKG (such as arginine, aspartate, lysine, and similar derivatives), other compounds that regulate nitric oxide in the cell including malondialdehyde (MDA) and asymmetric dimethylarginine (ADMA) and biologically active derivatives thereof.

A further embodiment of the invention comprises a method of sorting a sperm cell sample to form one or more subpopulations comprising the steps of providing a sperm cell sample, sorting the sperm cell sample to form one or more subpopulations and adding at least one OSR to the sperm cell sample during one or more of the aforementioned sorting steps, the concentration of the OSR being in the range of 0.01 mg/ml to 5 mg/ml.

An additional embodiment of the invention encompasses media used in processing sperm cells that comprise at least one OSR at the appropriate stock concentration to be present at a final processing concentration in the range of 0.01 mg/ml to 5 mg/ml in the sperm cell composition at the time of processing. A stress reducing media can be used for different processes including but not limited to sperm collection, artificial insemination, sperm sorting, in vitro fertilization, embryo culture, as well as sperm and embryo freezing. Media used in the sorting of sperm cells typically comprise one or more buffers and/or extenders (i.e., substances that preserve the viability and/or fertility of sperm cells).

Any buffer or buffer solution used in the processing of sperm can be used in the aforementioned media, including but not limited to phosphates, citrates, acetates, lactates, and combinations thereof, or a solution containing a salt, a carbohydrate, or a combination thereof can be employed in some of the embodiments of the invention, such as, but not limited to: Tris, TES, HEPES, TALP, TCA, PBS, citrate, milk and derivatives thereof, as discussed in detail in U.S. Pat. No. 7,208,265 the contents of which is hereby incorporated by reference in its entirety.

Any extender used in the processing of sperm can be used in the aforementioned media, including but not limited to energy sources, protein sources and antibiotics and may include one or more of the following: mono- and disaccharides, such as fructose, glucose, mannose, sucrose, and lactose; protein sources, such as egg yolk, milk, BSA and derivatives thereof; and any one of the commonly known antimicrobial or antibiotic agents, such as gentamicin, lincomycin, spectinomycin, their derivatives, or any combination thereof.

As used herein, the term "extender" may also include certain organic substances such as disaccharides, trisaccharides, and any combination thereof, egg yolk, milk, albumin, lecithin, cholesterol, their derivatives and any combination thereof. An extender may also include a detergent that may be an alkyl ionic detergent, such as sodium dodecyl sulfate (SDS).

A further embodiment of the present invention provides a method of improving the motility, viability and/or fertility of a sperm cell sample that has already undergone a sorting process, including but not limited to sex sorting, comprising the step of adding at least one OSR in the concentration range of 0.01 mg/ml to 5 mg/ml to a sorted sperm cell sample to form a sperm cell composition.

Accordingly, the present invention resides broadly in the use of a sperm cell composition, that in some embodiments comprise a sorted sperm cell sample and at least one OSR in the range of 0.01 mg/ml to 5 mg/ml, for use in ART. A further embodiment encompasses a sperm cell composition comprising sorted sperm cells, at least one OSR in the concentration range of 0.01 mg/ml to 5 mg/ml and a catch media (i.e., media found in the vessel that receives, or catches, the sorted sperm at the end of the sorting process). Another embodiment encompasses a sperm cell composition comprising a processed or sorted sperm cell sample, an OSR in the concentration range of 0.01 mg/ml to 5 mg/ml, and a cryoprotectant. An additional embodiment of the invention encompasses a frozen or vitrified sperm cell composition comprising a processed or sorted sperm cell sample, and at least one OSR in the concentration range of 0.01 mg/ml to 5 mg/ml.

Another broad object of the present invention is to improve the motility, viability (including longevity and ability to survive environmental stress) and fertility of processed and/or sorted sperm cells for use in ART such as IVF, AI, ICSI (as well as other techniques using enucleated cells), and MOET (as well as other embryo transfer techniques).

Accordingly, some of the embodiments of the present invention incorporate the use of sex sorted sperm cells that have had an OSR in the concentration range of 0.01 mg/ml to 5 mg/ml added to them in ART.

Accordingly, other embodiments of the present invention incorporate the use of a sperm cell composition, a sorted sperm cell sample, and at least one OSR in the concentration range of 0.01 mg/ml to 5 mg/ml, in ART.

One specific embodiment of the invention comprises a method of increasing the percentage of zygotes that develop into embryos in a given sample in a given amount of time, as well as increasing the percentage of embryos that are suitable for cryopreservation (i.e., the percentage of embryos that are blastocysts, expanded and hatching blastocysts, and hatched blastocysts), by mixing an egg with a sorted sperm cell sample that has been treated with at least one OSR in the concentration range of 0.01 mg/ml to 5 mg/ml.

A further embodiment of the invention resides in a method of making an embryo comprising mixing at least one egg with at least one sperm cell treated with at least one OSR in the concentration range of 0.01 mg/ml to 5 mg/ml. The embryos produced by this method constitute a further embodiment of the invention.

Other embodiments of the invention also include, a method for inseminating an organism through an AI technique using a processed or sorted sperm cell sample treated with at least one OSR in the concentration of 0.01 mg/ml to 5 mg/ml. The progeny of the organism that results from the aforementioned AI method also constitutes an embodiment of the invention. Furthermore, one embodiment of the invention encompasses a method for recovering embryos that are produced from the aforementioned AI method.

Embodiments of the invention can include sperm cells, or spermatozoa, collected from numerous species of male mammals, and the invention should be understood not to be limited to the species of male mammals described by the specific examples within this application. Rather the specific examples within this application are intended to be illustrative of the varied and numerous species of male mammals from which semen can be collected and utilized in certain embodiments of the invention. Embodiments of the invention, for example, may include the sperm cells of humans as well as animals having commercial value for meat or dairy production such as swine, ovine, bovine, equine, deer, elk, buffalo, or the like (naturally the mammals used for meat or dairy production may vary from culture to culture). It may also include the sperm cells of various domesticated mammalian species encompassed by canines and felines, as well as sperm cells of primates, including but not limited to chimpanzees, gorillas, or humans and the spermatozoa from whales, dolphins and other marine mammals. It may also include frozen-thawed sperm cells from all the various mammals above-described and further, including but not limited to, the sperm cells of deceased donors, from rare or exotic mammals, zoological specimens, or endangered species.

BRIEF DESCRIPTION OF THE DRAWINGS

In order that the invention may be more clearly understood, preferred embodiments of the present invention will now be described by way of example only with reference to the accompanying sheets of drawings wherein:

FIG. 4 is a graphical representation of the percent blastocysts and percent hatching found in Table 5.

FIG. 5 is a graphical representation of the percent motile sperm found in Table 1.

FIG. 6 is a graphical representation of the percent progressively motile sperm found in Table 1.

DETAILED DESCRIPTION OF THE INVENTION

Figure 1:
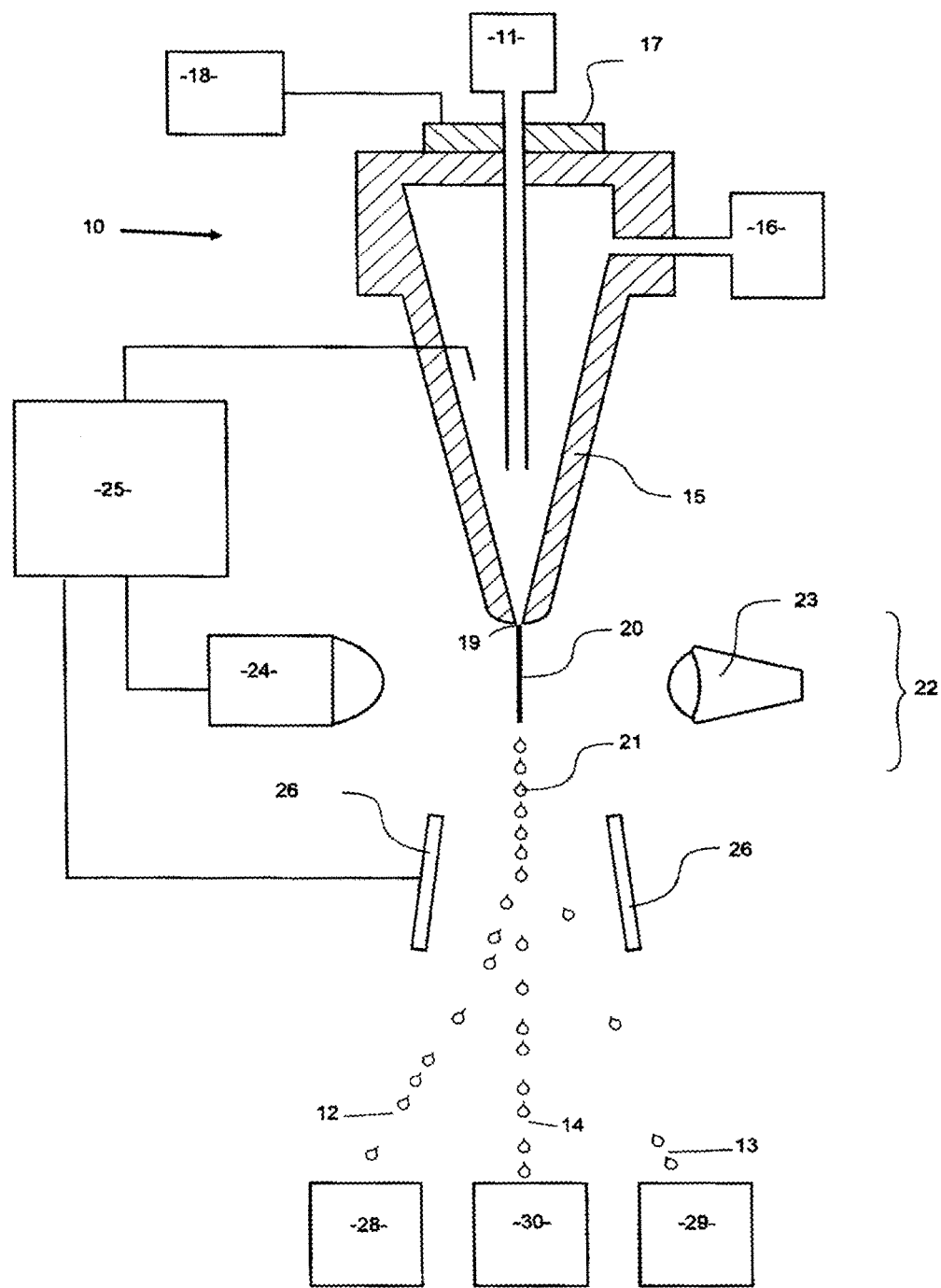
FIG. 1 is a schematic representation of part of a flow cytometer illustrating a method of sorting a sperm cell sample into one or more subpopulations according to some embodiments of the present invention.

In one aspect of the present invention, FIG. 1 illustrates in schematic form part of a flow cytometer used in a method to sort a sperm cell sample to form one or more subpopulations, the flow cytometer being generally referenced 10. In this particular embodiment sex sorting is taking place so the subpopulations are X-chromosome bearing sperm cells and Y-chromosome bearing sperm cells. FIG. 1 represents a single technique for sorting semen, but any known technique for sorting cells known in the art can be used with certain embodiments of the invention. Additional details of the basic sperm sorting apparatus and methodology are described in U.S. Pat. Nos. 5,135,759 and 7,371,517, the contents of which are hereby incorporated by reference in their entireties.

Once a sperm cell sample has been collected it can be extended as soon after collection with an extender that includes one or more antioxidants or vitamins. The sample is then typically held at a temperature of about 5° C. for between about 12 hours to about 18 hours while it is being shipped from the collection point to the flow cytometer 10 for the sorting process. This holding temperature can be in the range of between 4° C. and 39° C. and is commonly in the range of 4° C. and 16° C.

Upon arrival at the flow cytometer, the sample is stained with a DNA selective dye and a quenching dye to form a stained sperm cell sample and subsequently placed into a sperm cell source 11 of the flow cytometer 10. The flow cytometer 10 can be programmed by an operator to generate two charged droplet streams, one containing X-chromosome bearing sperm cells, charged positively, 12, one containing Y-chromosome bearing sperm cells, charged negatively 13 while an uncharged undeflected stream of dead cells 14 simply goes to waste.

An operator may also choose to program the flow cytometer in such a manner, that both the X- and Y-chromosome bearing sperm are collected using a "high purity sort" (in other words only live X- and Y-chromosome bearing sperm are collected) or to program the flow cytometer to collect both the X- and Y-chromosome bearing sperm using an "enriched sort" (in other words it will collect droplets containing live that were not previously sorted and excluding all initial dead again by the use of Boolean Gate logic available with the computer that controls the flow cytometer). The Boolean Gate logic can also be used to collect only one of either the X- or Y-chromosome bearing sperm.

Initially, a stream of sperm cells under pressure, is deposited into the nozzle 15 from the sperm cell source 11 in a manner such that they are able to be coaxially surrounded by a sheath fluid supplied to the nozzle 15 under pressure from a sheath fluid source 16. An oscillator 17 which may be present can be very precisely controlled via an oscillator control mechanism 18, creating pressure waves within the nozzle 15 which are transmitted to the coaxially surrounded sperm cell stream as it leaves the nozzle orifice 19. As a result, the exiting coaxially surrounded sperm cell stream 20 could eventually and regularly form droplets 21.

The charging of the respective droplet streams is made possible by the cell sensing system 22 which includes a laser 23 which illuminates the nozzle exiting stream 20, and the light emission of the fluorescing stream is detected by a sensor 24. The information received by the sensor 24 is fed to a sorter discrimination system 25 which very rapidly makes the decision as to whether to charge a forming droplet and if so which charge to provide the forming drop and then charges the droplet 21 accordingly.

A characteristic of X-chromosome bearing sperm is that they tend to absorb more fluorochrome dye than Y-chromosome bearing sperm and as such, the amount of light emitted by the laser excited absorbed dye in the X-chromosome bearing sperm differs from that of the Y-chromo-some bearing sperm and this difference in characteristic tells the sorter discrimination system 25 which charge to apply to droplets containing only X- or only Y-chromosome bearing sperm cells. Dead cells (or those about to die) have absorbed the quenching dye and the sorter discrimination system 25 does not charge droplets containing such cells.

The charged or uncharged droplet streams then pass between a pair of electrostatically charged plates 26, which cause them to be deflected either one way or the other or not at all depending on their charge into respective collection vessels 28 and 29 to form respectively a gender enriched population of X-chromosome bearing and a gender enriched population of Y-chromosome bearing sperm cells having a DNA selective dye associated with their DNA. The uncharged non-deflected stream containing a sub-population of dead cells (or those that are about to die) go to the waste container 30.

The collected sex sorted sperm cells may then be frozen and stored or frozen and sent on for further processing (or simply used for further processing immediately), further processing meaning for example, the purposes of research or for use in ART such as IVF, AI, ICSI (as well as other techniques using enucleated cells), and MOET (as well as other embryo transfer techniques).

In alternative embodiments not illustrated, the catch media contained in the otherwise empty collection vessels may also contain OSR in the concentration range of 0.01 mg/ml to 5 mg/ml. The OSR may be added during this stage of the sorting process (be it sex sorting or other form of sorting) and/or in addition to another method step in the sorting (be it sex sorting or other form of sorting) process.

Furthermore, in the alternative embodiments, the OSR administered in the concentration range of 0.01 mg/ml to 5 mg/ml to the sperm cell sample or composition can be added to the DNA selective dye and/or the quenching dye solutions. Some embodiments include use of one or more OSRs as pre-mixed components of the prepared buffers, extenders, stains, catch fluids, and/or cryo-extenders used in the sex sorting procedure. Accordingly, the OSR may be added to the sperm cell sample at one or more steps during sex-sorting, including when the sperm cell sample is being first handled following collection, and/or stained with a DNA selective dye and/or the quenching dye, and/or at the time of collection from the flow cytometer, and/or later when preparing the sample for cryopreservation by adding the OSR or OSR cocktail to the cryoextender.

Likewise, some sorting embodiments include sorting of frozen-thawed conventional semen whereby the OSR can be added to the thawed semen sample shortly after thawing and then reverse sorted to produce sex-sorted sperm cell subpopulations which include the addition of an OSR at one or more steps during the extended processing procedure of gender selection.

In some cases, when the sorting of sperm cells is not going to involve sex sorting, a quenching dye without the need for a DNA staining dye may be required, in which case the OSR will only be present in the quenching dye to form the stained sample. In this way, depending on the embodiment chosen, the OSR may again only be added during this stage of the sorting process (be it sex sorting or other form of sorting) or in addition to at least one other method step in the sorting (be it sex sorting or other form of sorting) process.

Again, in the alternative embodiments, the collected sex sorted sperm cells (or in alternative embodiments the sorted, i.e. non-sex sorted sperm cell samples) once frozen will, prior to such further processing, require to be thawed. Either before freezing or upon thawing, the antioxidant, again in the concentration range of 0.01 mg/ml to 5 mg/ml, may be added to the sample before freezing and/or to the thawed sample. In this way, depending on the embodiment chosen, the OSR may again only be added during this stage of the sorting process (be it sex sorting or other form of sorting) or in addition to at least one other method step in the sorting (be it sex sorting or other form of sorting) process.

In yet further alternative embodiments the time period allowed to elapse after the addition of the OSR, can vary and may be in the range of about 5 seconds to about 72 hours (excluding freezing time and time spent in the freezer or in the cryopreserved state), the lower end of the scale providing for almost immediate sorting of the sperm sample while the upper end of the scale would cover the typical maximum time frame associated with moving a sperm sample from its collection point to its sorting point. This is usually a flight and/or road travel time. More particularly, the time periods may be about 5 seconds to about 3 hours; about 3 hours to about 6 hours; about 6 hours to about 12 hours; about 12 hours to about 18 hours; about 18 hours to about 24 hours; about 24 hours to about 36 hours; about 36 hours to about 48 hours; about 48 hours to about 60 hours; and about 60 hours to about 72 hours; and.

Another alternative embodiment may include the use of an extender within a pH range of 5.5 to 7.8, and frequently at about 6.5; about 6.6; about 6.7; about 6.8; about 6.9; about 7.0; about 7.1; about 7.2; about 7.3; about 7.4; or about 7.5.

As described in the illustrated embodiment, different steps of the method are carried out at different temperatures. In alternative embodiments, at least one of the method steps is carried out within a temperature range selected from the group consisting of about 5° C. to about 15° C.; about 15° C. to about 20° C.; about 20° C. to about 25° C.; about 25° C. to about 30° C.; about 30° C. to about 35° C.; about 35° C. to about 40° C. and about 40° C. to about 45° C. This allows for different steps in the sorting method to be performed within different temperature ranges.

In another aspect of the present invention there is provided a method of treating the motility of sperm cells in a sperm cell sample. In this embodiment, the sperm cell sample, which may be a gender enriched population of X-chromosome bearing or Y-chromosome bearing sperm cells having a DNA selective or DNA binding dye associated with their DNA, a sample sorted into one or more subpopulations or a conventional non-sorted sample, the method of treating the motility of the sperm cells in the sperm cell sample comprises the step of adding an OSR in the concentration range of 0.01 mg/ml to 5 mg/ml to the sperm cell sample to form a sperm cell composition (and in this embodiment at a concentration of 0.5 mg/ml). The OSR which is added forms part of an extender which is in a pH range of 6.5 to 7.5 and in particular embodiments, the pH is selected from the group consisting of about 6.5; about 6.6; about 6.7; about 6.8; about 6.9; about 7.0; about 7.1; about 7.2; about 7.3; about 7.4; and about 7.5.

After the addition of the antioxidant, a time period being in the range of about 5 seconds to about 72 hours is allowed to elapse before the sample undergoes further processing in the form of for example, research or for use in assisted reproductive technologies such as IVF, AI, ICSI (as well as other techniques using enucleated cells), and MOET (as well as other embryo transfer techniques). The time period which is allowed to elapse may be selected from the range consisting of: about 5 seconds to about 3 hours; about 3 hours to about 6 hours; about 6 hours to about 12 hours; about 12 hours to about 18 hours; about 18 hours to about 24 hours; about 24 hours to about 36 hours; about 36 hours to about 48 hours; about 48 hours to about 60 hours; and about 60 hours to about 72 hours. The techniques for fertilizing an egg involve the added step of mixing at least one egg with the sperm cell sample. Any conventional technique such as those listed above can be used with the invention, including any conventional IVF or AI technique. Typical IVF techniques are disclosed in WO/0243486, for example, which is incorporated by reference herein in its entirety. Typical AI techniques are disclosed in U.S. Pat. No. 6,149,867, for example, which is incorporated by reference herein in its entirety.

In alternative embodiments, the sperm cell sample may have been a frozen sample that has been allowed to thaw. The method may further comprise the step of staining the sperm cell sample or the sperm cell composition with a DNA selective dye if the sample is not a sex sorted sample.

The method may also comprise the step of freezing the sperm cell composition to form a frozen sperm cell composition that may be allowed to thaw. At least one of the method steps in this second aspect of the present invention is carried out within a temperature range selected from the group consisting of about 0° C. to about 5° C.; about 5° C. to about 15° C.; about 15° C. to about 20° C.; about 20° C. to about 25° C.; about 25° C. to about 30° C.; about 30° C. to about 35° C.; about 35° C. to about 40° C. and about 40° C. to about 45° C. Thus, each method step may be carried out at a different or similar temperature range.

Suggested Methods

By way of example, the following oocyte maturation procedure, IVF procedure, in vitro culture procedure and co-culture procedure may be used with the invention. One skilled in the art will know that variations on these methods exist and that these methods should not be construed to limit the functionality of the current invention. These methods are illustrative only.

1. Oocyte Collection.

Collect slaughterhouse oocytes, wash 1× with about 3 mL Hepes washing media and with 1× with TCM-199 (Invitrogen, Carlsbad, Calif.)+10% Fetal Bovine Serum (FBS). Culture in maturation media for 22 hrs in a $CO_2$ incubator at 38.5° C. In one embodiment, the maturation media contains TCM-199, FBS, pyruvate, chorionic gonadotropin (e.g., Chorulon (Intervet, Summit N.J.)), follicle stimulating hormone (FSH) (e.g., Folltropin (Bioniche, Belleville, Canada)), estradiol, and at least one antibiotic. In a further embodiment, Amikacin (Sigma-Aldrich, St. Louis, Mo.) can be used as the antibiotic. In another embodiment, the maturation media may also comprise luteinizing hormone.

In one embodiment, the maturation media may comprise 5-20 ml of TCM-199 Earl's; 0.5-2 ml of FBS (Thermo Fisher Scientific, Waltham, Mass.); 10-30 μl of pyruvate (prepared by adding 0.05-0.20 g of sodium pyruvate (Sigma-Aldrich, St. Louis, Mo.) to 5-20 ml of saline solution); 50-200 μl of chorionic gonadotropin (prepared by adding 5-20 UI of Chorulon (Intervet, Summit N.J.) to 5-20 ml of TCM-199 Earl's); 5-20 μl of FSH (prepared by adding 0.001-0.01 g of Folltropin (Bioniche, Belleville, Canada) to 5-20 ml of TCM-199 Earl's); 5-20 μl of estradiol (prepared by adding 0.001-0.05 g of estradiol (Sigma-Aldrich, St. Louis, Mo.) to 5-20 ml of Etanol (Sigma-Aldrich, St. Louis, Mo.)); and 10-30 μl Amikacin (prepared by adding 0.1-1 g Amikacin sulfate salt (Sigma-Aldrich) to 20-40 ml of saline solution). In alternative embodiments, the maturation media may comprise the aforementioned components using different volumes but in the same proportion to each other, e.g., in one embodiment, the maturation media may comprise 10-40 ml of TCM-199; 1-4 ml of FBS; 20-60 μl of sodium pyruvate, etc. In a further embodiment, the maturation media comprises the above preparations of TCM-199 Earl's, FBS, pyruvate, chorionic gonadotropin, FSH, estradiol and an antibiotic in the approximate ratio of 9:1:0.02:0.1:0.01:0.01:0.02 by volume, respectively.

2. In Vitro Fertilization.

Trim away cumulus cells from matured oocytes. Transfer them to a fertilization dish and return to the $CO_2$ incubator. Thaw frozen semen straws using standard procedures, centrifuge in 800 μL of Pure Sperm gradient (Nidacon, Molndal, Sweden), or a percoll or similar gradient at 2500 RPM for 10 minutes to remove egg components, glycerol and other debris. Remove supernatant, leaving a loose pellet of live sperm. Combine pellets using a small amount of fertilization media and repellet at 1500 RPM for 3 minutes. Carefully remove supernatant. Then gently mix the pellet. After determining the desired insemination dose, inseminate the oocytes by adding sperm to the pellet, then culture in a dish and return to the $CO_2$ incubator for about 18-22 hours.

3. In Vitro Culture.

Remove presumptive zygotes from the fertilization dish and transfer into a sterile 1.5 mL eppendorf tube. Allow zygotes to form a loose pellet and remove excess media to form a 1:1 ratio of pellet and solution. Rinse the eppendorf tube with TCM-199, place contents into a dish and wash with BSA media. Then culture presumptive zygotes (discard disfigured oocytes, as well as oocytes with yellow colored cytoplasm or vacuolated cytoplasm) in a dual gas incubator (5% $CO_2$, 5% $O_2$) at 38.5° C. for about 48 hours.

4. Co-Culture.

Transfer cleaved zygotes to co-culture dishes comprising the cumulus cells from the mature oocytes and FBS media topped with mineral oil, and incubate in a $CO_2$ incubator at 38.5° C. until needed.

5. Sperm Motility Evaluations by CASA.

A comparison of viewing chambers and slides can be done in a variety of IVOS instruments, which for example only can be a Hamilton-Thorne IVOS (Hamilton-Thorne, Beverly, Mass.). Instrument settings: image capture; frames per second=60; number of frames=30; cell detection; minimum contrast=50; minimum cell size=5; defaults, cell size=5; cell intensity=50; progressive cells, path velocity=50 um/s; straightness>70%; slow cells (um/s); average path velocity (VAP, <30 um/s), straight-line velocity (VSL, <15 um/s). The CASA motility variables measured can be a percentage of total motile sperm (motile), percentage of progressively motile sperm (progressive), VAO, VSL, curvilinear velocity (VCL, um/s), average lateral head displacement (ALK, um) and the number of times the sperm head crosses the mean path/s (BCF, Hz), straight-line sperm motility (STR, %), and linear sperm motility (LIN, %). See for instance, Lenz, R W, et al., J Anim Sci (2011) 89:383-388, incorporated by reference herein in its entirety.

A further aspect of the present invention entails the use of a sperm cell sample treated with an OSR in AI. AI in the present invention includes a method whereby a fresh or frozen thawed sperm cell sample is used to inseminate by way of passage of the semen or sperm sample into the female reproductive tract, with or without an accessorizing tool such as an AI gun, catheter or pipette.

Frozen semen samples may be contained in semen straws, which are thawed before the AI procedure using standard methods. In certain embodiments of the invention, the semen straws contain about 0.25-0.5 ml of fluid and are often sufficient for a single insemination.

To increase the number of offspring that a female can produce, embryo transfer techniques (such as MOET) have been developed and are well known to those skilled in the art. Conventional embryo transfer techniques include injection of females with suitable hormones that cause them to produce multiple eggs (oocytes) in a single estrous cycle. This process is often referred to as superovulation. Each female is then artificially inseminated with a sperm cell sample from a male that is either fresh or has been cryopreserved.

In another aspect of the invention, zygotes and/or embryos from artificially inseminated females can be recovered and then cultured and/or cryopreserved/vitrified.

Example 1

Figure 2:
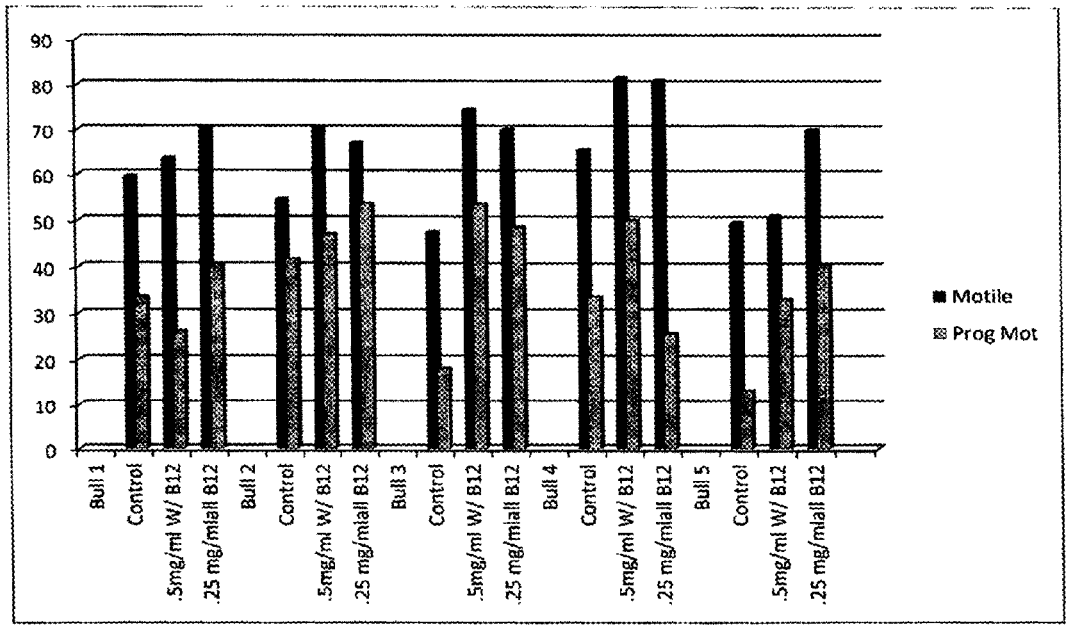
FIG. 2 illustrates a graphical representation of the motility and progressive motility found in Table 1.
Figure 3:
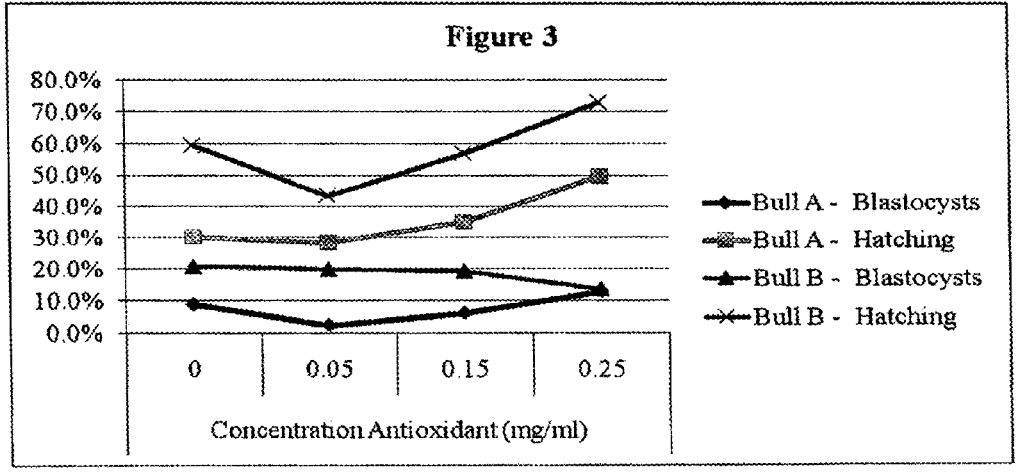
FIG. 3 is a graphical representation of the percent blastocysts and percent hatching found in Table 4.

One set of semen from each bull was used as a control while to the remaining sets of semen samples were added vitamin B12, as the antioxidant, at respective concentrations of 0.5 mg/ml and 0.25 mg/ml. For each sample, the same concentration of vitamin B12 was added (i) during the staining process, and (ii) in the catch fluid of the collection vessel. Control samples did not contain vitamin B12. Sperm samples were sorted in "High Purity" mode, and the collected sex-sorted sperm were extended with a cryoextender, which in some cases again contained the same concentration of vitamin B12 and the samples were frozen. Three hours after thawing (which is a standard time frame to conduct quality control assessments on sorted frozen thawed sperm samples) the thawed samples were put through CASA, a machine that provides various data on sperm including motility and progressive motility information. The results are shown below in Table 1 and the motility and progressive motility are graphically represented in FIG. 2.

In the tables below: VAP (average path velocity (μm/s)); VSL (straight-line velocity (μm/s)); VCL (curvilinear velocity (μm/s)); ALH (average lateral head displacement (μm)); BCF (the number of times the sperm head crosses the mean path/s in Hz); STR (percent straight-line sperm motility); LIN (percent linear sperm motility); PIA (percent intact acrosomes); motile (percent motile sperm); and progressive (percent progressively motile sperm).

The two step addition results represent treatments with vitamin B12 present at the same indicated concentration in the catch fluid of the collecting vessel and in the cryoprotectant extender prior to freezing the sample only (2 step-freeze; − + +); the three step addition results indicate that the same concentration of vitamin B12 was added during the staining step, the collecting step (in the catch fluid of the collecting vessel) and in the cryoprotectant extender prior to freezing the sample (3 step). There is no correlation with regard to randomly assigned names such as "Bull A." Bull A from Example 5 is not the same bull as Bull A from Example 7.

TABLE 1

| | Motility (2 step and 3 step) (3 hrs Post-Thaw) | | | | | | | | | | |
|---|---|---|---|---|---|---|---|---|---|---|---|
| | Total cells | Motile (%) | Prog Mot (%) | VAP (μm/s) | VSL (μm/s) | VCL (μm/s) | ALH (μm) | BCF (Hz) | STR (%) | LIN (%) | PIA (%) |
| Bull 1 | | | | | | | | | | | |
| Control | 562 | 59.5 | 33.5 | 54 | 47 | 95.5 | 4 | 21.5 | 87.5 | 51 | 73.5 |
| 0.5 mg/ml, 2 step F | 925 | 63.5 | 26 | 56 | 45 | 94 | 4 | 23 | 86.5 | 49 | 74 |
| 0.25 mg/ml, 3 step | 815 | 70.5 | 40.5 | 55 | 48 | 92 | 4 | 23.5 | 87.5 | 53 | 83 |
| Bull 2 | | | | | | | | | | | |
| Control | 529 | 54.5 | 41.5 | 61 | 53.5 | 107.5 | 4.5 | 23 | 87.5 | 51.5 | 64 |
| 0.5 mg/ml, 2 step F | 269 | 70.5 | 47 | 77 | 66 | 108 | 4 | 21.5 | 85.5 | 61 | 84 |
| 0.25 mg/ml, 3 step | 693 | 67 | 53.5 | 68 | 55 | 111.5 | 4.5 | 24 | 87 | 51 | 79.5 |
| Bull 3 | | | | | | | | | | | |
| Control | 599 | 47.5 | 18 | 49.5 | 42.5 | 84.5 | 4 | 20.5 | 86.5 | 51.5 | 52.5 |
| 0.5 mg/ml, 2 step F | 800 | 74.5 | 53.5 | 56 | 51 | 98 | 4 | 22.5 | 84.5 | 52.5 | 87 |
| 0.25 mg/ml, 3 step | 656 | 70 | 48.5 | 59 | 50 | 101 | 4 | 24 | 85.5 | 51 | 80 |

TABLE 1-continued

| | Motility (2 step and 3 step) (3 hrs Post-Thaw) | | | | | | | | | | |
|---|---|---|---|---|---|---|---|---|---|---|---|
| | Total cells | Motile (%) | Prog Mot (%) | VAP (µm/s) | VSL (µm/s) | VCL (µm/s) | ALH (µm) | BCF (Hz) | STR (%) | LIN (%) | PIA (%) |
| Bull 4 | | | | | | | | | | | |
| Control | 602 | 65.5 | 33.5 | 53.5 | 45.5 | 89.5 | 4 | 23.5 | 86 | 52.5 | 72.5 |
| 0.5 mg/ml, 2 step F | 874 | 81.5 | 50 | 60 | 53 | 109 | 5 | 26 | 83.5 | 49 | 88 |
| 0.25 mg/ml, 3 step | 1059 | 81 | 25.5 | 43 | 51 | 88.5 | 5 | 23 | 82.5 | 47 | 86 |
| Bull 5 | | | | | | | | | | | |
| Control | 638 | 49.5 | 13 | 45.5 | 38.5 | 86.5 | 5 | 18 | 84 | 45.5 | 63.5 |
| 0.5 mg/ml, 2 step F | 842 | 51 | 33 | 50 | 47 | 101 | 5 | 20.5 | 84 | 47 | 79 |
| 0.25 mg/ml, 3 step | 787 | 70 | 40.5 | 61 | 48 | 106.5 | 5 | 21.5 | 84.5 | 47 | 80 |

Example 2

In another series of experiments, the CASA results regarding motility and progressive motility after 4.5 hours after thawing sex-sorted samples against a control are shown below in Table 2. The (2 step-freeze) results indicate that vitamin B12 at the same concentration was present in the catch fluid of the collecting vessel and in the cryoprotectant extender prior to freezing the sample; the (3 step) results indicate that the same concentration of vitamin B12 was added during the staining step, the collecting step (in the catch fluid of the collecting vessel) and in the cryoprotectant extender prior to freezing the sample.

With respect to "Bull A," the two sets of results shown were obtained on two different days using thawed samples from the same initially sorted batch of sperm. In both cases the concentration of the vitamin B12 was 1 mg/ml. For all other bulls in the table below unless otherwise indicated, the concentration of vitamin B12 added was also 1 mg/ml.

TABLE 2

| | Motility (4.5 hrs Post-Thaw) | | |
|---|---|---|---|
| | Total cells | Motile | Progressive |
| Bull A | | | |
| control | 322 | 38 | 0 |
| 1 mg/ml - 2 step-F | 250 | 41 | 8 |
| 1 mg/ml - 3 step | 287 | 64 | 37 |
| Bull A (day 2) | | | |
| control | 328 | 46 | 4 |
| 1 mg/ml - 2 step-F | 433 | 71 | 31 |
| 1 mg/ml - 3 step | 487 | 64 | 11 |
| Bull B | | | |
| control | 298 | 33 | 1 |
| 1 mg/ml - 2 step-F | 316 | 22 | 1 |
| 1 mg/ml - 3 step | 237 | 59 | 19 |
| Bull C | | | |
| control | 403 | 52 | 1 |
| 1 mg/ml - 2 step-F | 432 | 76 | 43 |
| 1 mg/ml - 3 step | 613 | 62 | 2 |
| Bull D | | | |
| control | 644 | 37 | 3 |
| 1 mg/ml - 3 step | 400 | 59 | 9 |
| Bull E | | | |
| control | 653 | 41 | 1 |
| 1 mg/ml - 3 step | 648 | 52 | 1 |
| Bull F | | | |
| control | 638 | 39 | 7 |
| 0.5 mg/ml - 3 step | 761 | 51 | 16 |
| 0.25 mg/ml - 3 step | 730 | 60 | 23 |
| Bull G | | | |
| control | 588 | 41 | 13 |
| 0.5 mg/ml - 3 step | 162 | 65 | 57 |
| 0.25 mg/ml - 3 step | 1003 | 56 | 32 |

Example 3

In an additional experiment, motility and progressive motility were checked 3.75 hours after thawing a sex sorted semen sample treated with the antioxidant. The OSR was not added to the control sample. The semen sample was derived from a single bull. 0.25 mg/ml concentration of vitamin B12 was added to the test sample during the staining step, the collecting step (in the catch fluid of the collecting vessel) and in the cryoprotectant extender prior to freezing the sample. The results are shown in Table 3 below.

TABLE 3

| Bull 1 | Motility (3.75 hrs Post-Thaw) | | | | | | | | | | |
|---|---|---|---|---|---|---|---|---|---|---|---|
| | Total cells | Motile (%) | Prog Mot (%) | VAP (μm/s) | VSL (μm/s) | VCL (μm/s) | ALH (μm) | BCF (Hz) | STR (%) | LIN (%) | PIA (%) |
| Control | 452 | 7 | 0 | 37 | 28 | 71 | 3 | 16 | 74 | 40 | 41 |
| 0.25 mg/ml, 3 step | 536 | 39 | 5 | 40 | 34 | 76 | 5 | 17 | 85 | 45 | 70 |

Example 4

An experiment was designed to test the effect of OSR treated sperm cells on the development of eggs fertilized with those sperm cells. In this experiment, bull semen from two bulls was sex sorted with flow cytometry, with vitamin B12 present at equal concentrations in the media used to stain the sperm cells, in the catch fluid of the collecting vessel and in the cryoprotectant extender prior to freezing the sex sorted sample (3 step). For each bull, three different concentrations of vitamin B12 were tested: 0.05 mg/ml, 0.15 mg/ml and 0.25 mg/ml. The control samples were not treated with vitamin B12.

Slaughterhouse oocytes were collected and washed 1× with about 3 mL Hepes washing media and with 1× with TCM-199+10% FBS. The oocytes were then cultured in maturation media for 22 hrs in a $CO_2$ incubator at 38.5° C. Cumulus cells were trimmed away from matured oocytes, transferred to a fertilization dish, and returned to the $CO_2$ incubator.

Frozen semen straws were thawed using standard procedures and centrifuged in 800 μL of Pure Sperm gradient at 2500 RPM for 10 minutes in order to remove egg, glycerol and other debris. The supernatant was removed, leaving a loose pellet of live sperm. Pellets were combined using a small amount of fertilization media and repelleted at 1500 RPM for 3 minutes. The supernatant was then carefully removed and the pellet gently mixed. After determining the desired insemination dose, the matured oocytes were then inseminated by adding sperm to the pellet, cultured in a dish and returned to the $CO_2$ incubator for about 18-22 hours.

Presumptive zygotes were removed from the fertilization dish and transferred into a sterile 1.5 ml eppendorf tube. The zygotes were allowed to form a loose pellet and excess media was removed to form a 1:1 ratio of pellet and solution. The eppendorf tube was vortexed for 90 seconds and then rinsed with TCM-199. The contents were placed into a dish and then washed with BSA media. The presumptive zygotes were then cultured in a dual gas incubator (5% $CO_2$, 5% $O_2$) at 38.5° C. for about 48 hours. Cleaved zygotes were then transferred to co-culture dishes comprising the cumulus cells from the mature oocytes and FBS media topped with mineral oil and incubated in a $CO_2$ incubator at 38.5° C.

Embryos were observed 7 days after IVF to check: Zyg (the number of zygotes put into culture); 4-2C (the number of zygotes that underwent the 2 cell to 4 cell transition 48 hours after IVF); 8C (the number of zygotes with 8 cells 48 hours after IVF); 8C % (the percentage of zygotes having 8 cells 48 hours after IVF); % Clv (percent cleaved 48 hours after IVF); C1 (number of expanded and hatching and hatched blastocysts 7 days after IVF); C1- (number of blastocysts 7 days after IVF); and C2 (number of early blastocysts and compact morulas 7 days after IVF), Total Embs (total number of blastocysts=C1+C1-+C2); Blast % (percent of cultured zygotes resulting in blastocyst formation); Hatch # (the number of embryos shedding the zona palucida in preparation for implantation observed at 8.5 days after IVF); and Hatch % (percentage of embryos that shed the zona). The results are provided in Table 4 below.

TABLE 4

| | IVF - Embryo/Fertilization (3 step) | | | | | | | | | | | |
|---|---|---|---|---|---|---|---|---|---|---|---|---|
| | Zyg | 4-2C | 8C | 8C % | % Clv | C1 | C1- | C2 | Total Embs | Blast % | Hatch # | Hatch % |
| Bull A | | | | | | | | | | | | |
| Control | 96 | 36 | 8 | 8.3 | 45.8 | 1 | 0 | 5 | 6 | 6.3 | 2 | 33.3 |
| Control | 68 | 19 | 7 | 10.3 | 38.2 | 0 | 0 | 2 | 2 | 2.9 | 0 | 0.0 |
| Control | 91 | 31 | 19 | 20.9 | 54.9 | 2 | 3 | 10 | 15 | 16.5 | 5 | 33.3 |
| Total/Avg | 255 | 86 | 34 | (13.3) | (47.1) | 3 | 3 | 17 | 23 | (9.0) | 7 | (30.4) |
| 0.05 mg/ml | 87 | 20 | 3 | 3.4 | 26.4 | 0 | 0 | 1 | 1 | 1.1 | 0 | 0.0 |
| 0.05 mg/ml | 95 | 26 | 9 | 9.5 | 36.8 | 1 | 0 | 1 | 2 | 2.1 | 1 | 50.0 |
| 0.05 mg/ml | 94 | 20 | 11 | 11.7 | 33.0 | 0 | 3 | 1 | 4 | 4.3 | 1 | 25.0 |
| Total/Avg | 276 | 66 | 23 | (8.3) | (32.2) | 1 | 3 | 3 | 7 | (2.5) | 2 | (28.6) |
| 0.15 mg/ml | 89 | 25 | 4 | 4.5 | 32.6 | 0 | 1 | 4 | 5 | 5.6 | 0 | 0.0 |
| 0.15 mg/ml | 90 | 29 | 9 | 10.0 | 42.2 | 1 | 0 | 4 | 5 | 5.6 | 3 | 60.0 |
| 0.15 mg/ml | 91 | 24 | 6 | 6.6 | 33.0 | 2 | 1 | 4 | 7 | 7.7 | 3 | 42.9 |
| Total/Avg | 270 | 78 | 19 | (7.0) | (35.9) | 3 | 2 | 12 | 17 | (6.3) | 6 | (35.3) |
| 0.25 mg/ml | 91 | 33 | 6 | 6.6 | 42.9 | 0 | 2 | 3 | 5 | 5.5 | 2 | 40.0 |

TABLE 4-continued

IVF - Embryo/Fertilization (3 step)

|  | Zyg | 4-2C | 8C | 8C % | % Clv | C1 | C1– | C2 | Total Embs | Blast % | Hatch # | Hatch % |
|---|---|---|---|---|---|---|---|---|---|---|---|---|
| 0.25 mg/ml | 93 | 38 | 20 | 21.5 | 62.4 | 4 | 2 | 10 | 16 | 17.2 | 10 | 62.5 |
| 0.25 mg/ml | 91 | 26 | 16 | 17.6 | 46.2 | 2 | 3 | 10 | 15 | 16.5 | 6 | 40.0 |
| Total/Avg | 275 | 97 | 42 | (15.3) | (50.5) | 6 | 7 | 23 | 36 | (13.1) | 18 | (50.0) |
| Bull B | | | | | | | | | | | | |
| Control | 91 | 15 | 35 | 38.5 | 54.9 | 3 | 3 | 8 | 14 | 15.4 | 9 | 64.3 |
| Control | 90 | 25 | 29 | 32.2 | 60.0 | 4 | 5 | 9 | 18 | 20.0 | 10 | 55.6 |
| Control | 92 | 20 | 33 | 35.9 | 57.6 | 7 | 6 | 12 | 25 | 27.2 | 15 | 60.0 |
| Total/Avg | 273 | 60 | 97 | (35.5) | (57.5) | 14 | 14 | 29 | 57 | (20.9) | 34 | (59.6) |
| 0.05 mg/ml | 90 | 18 | 40 | 44.4 | 64.4 | 2 | 4 | 13 | 19 | 21.1 | 9 | 47.4 |
| 0.05 mg/ml | 92 | 23 | 27 | 29.3 | 54.3 | 4 | 2 | 9 | 15 | 16.3 | 7 | 46.7 |
| 0.05 mg/ml | 93 | 22 | 27 | 29.0 | 52.7 | 5 | 3 | 13 | 21 | 22.6 | 8 | 38.1 |
| Total/Avg | 275 | 63 | 94 | (34.2) | (57.1) | 11 | 9 | 35 | 55 | (20.0) | 24 | (43.6) |
| 0.15 mg/ml | 96 | 21 | 38 | 39.6 | 61.5 | 6 | 7 | 10 | 23 | 24.0 | 17 | 73.9 |
| 0.15 mg/ml | 93 | 32 | 14 | 15.1 | 49.5 | 2 | 3 | 6 | 11 | 11.8 | 6 | 54.5 |
| 0.15 mg/ml | 100 | 21 | 29 | 29.0 | 50.0 | 4 | 4 | 14 | 22 | 22.0 | 9 | 40.9 |
| Total/Avg | 289 | 74 | 81 | (28.0) | (53.6) | 12 | 14 | 30 | 56 | (19.4) | 32 | (57.1) |
| 0.25 mg/ml | 92 | 24 | 34 | 37.0 | 63.0 | 5 | 3 | 11 | 19 | 20.7 | 14 | 73.7 |
| 0.25 mg/ml | 96 | 31 | 23 | 24.0 | 56.3 | 1 | 3 | 3 | 7 | 7.3 | 5 | 71.4 |
| Total/Avg | 188 | 55 | 57 | (30.3) | (59.6) | 6 | 6 | 14 | 26 | (13.8) | 19 | (73.1) |

Example 5

A similar experiment as done in Example 4 was done to test the effect of OSR treated sperm cells on the development of eggs fertilized using a higher concentration of the antioxidant, comparing it to one of the earlier used concentrations. Semen samples from two bulls of different breeds (one Holstein; one Jersey) were sex sorted using flow cytometry, again using vitamin B12 as the antioxidant, present at equal concentrations during staining, in the catch fluid of the collecting vessel and in the cryoprotectant extender prior to freezing the sex sorted sample (3 step). For each bull, the two concentrations of vitamin B12 tested were: 0.5 mg/ml and 0.25 mg/ml. The control samples were not treated with vitamin B12. All experimental steps were done the same as in Example 4. The results are shown in Table 5 below.

TABLE 5

IVF - Embryo Fertilization (3 step)

|  | Zyg | 4-2C | 8C | 8C % | % Clv | C1 | C1– | C2 | Total Embs | Blast % | Hatch # | Hatch % |
|---|---|---|---|---|---|---|---|---|---|---|---|---|
| Bull A (Holstein) | | | | | | | | | | | | |
| Control | 91 | 25 | 35 | 38.5 | 65.9 | 3 | 2 | 4 | 9 | 9.9 | 3 | 33.3 |
| Control | 93 | 40 | 19 | 20.4 | 63.4 |  | 1 | 2 | 3 | 3.2 | 0 | 0.0 |
| Control | 98 | 25 | 25 | 25.5 | 51.0 | 3 | 6 | 5 | 14 | 14.3 | 6 | 42.9 |
| Total/Avg | 282 | 90 | 79 | 28.0 | (60.1) | 6 | 9 | 11 | 26 | (9.2) | 9 | (34.6) |
| 0.25 mg/ml | 97 | 25 | 39 | 40.2 | 66.0 | 6 | 9 | 5 | 20 | 20.6 | 8 | 40.0 |
| 0.25 mg/ml | 97 | 34 | 30 | 30.9 | 66.0 | 5 | 6 | 5 | 16 | 16.5 | 4 | 25.0 |
| 0.25 mg/ml | 97 | 23 | 33 | 34.0 | 57.7 | 6 | 7 | 6 | 19 | 19.6 | 9 | 47.4 |
| Total/Avg | 291 | 82 | 102 | 35.1 | (63.2) | 17 | 22 | 16 | 55 | (18.9) | 21 | (38.2) |
| 0.5 mg/ml | 94 | 25 | 34 | 36.2 | 62.8 | 0 | 3 | 3 | 6 | 6.4 | 1 | 16.7 |
| 0.5 mg/ml | 95 | 29 | 30 | 31.6 | 62.1 | 1 | 7 | 7 | 15 | 15.8 | 4 | 26.7 |
| 0.5 mg/ml | 93 | 18 | 35 | 37.6 | 57.0 | 5 | 7 | 8 | 20 | 21.5 | 11 | 55.0 |
| Total/Avg | 282 | 72 | 99 | 35.1 | (60.6) | 6 | 17 | 18 | 41 | (14.5) | 16 | (39.0) |
| Bull B (Jersey) | | | | | | | | | | | | |
| Control | 97 | 39 | 39 | 40.2 | 80.4 | 5 | 5 | 3 | 13 | 13.4 | 7 | 53.8 |
| Control | 100 | 22 | 12 | 12.0 | 34.0 | 4 | 5 |  | 9 | 9.0 | 2 | 22.2 |
| Control | 100 | 22 | 29 | 29.0 | 51.0 | 2 | 5 | 1 | 8 | 8.0 | 3 | 37.5 |
| Total/Avg | 297 | 83 | 80 | 26.9 | (55.1) | 11 | 15 | 4 | 30 | (10.1) | 12 | (40.0) |
| 0.25 mg/ml | 94 | 25 | 45 | 47.9 | 74.5 | 5 | 9 | 4 | 18 | 19.1 | 12 | 66.7 |

TABLE 5-continued

| | | | | | IVF - Embryo Fertilization (3 step) | | | | | | | |
|---|---|---|---|---|---|---|---|---|---|---|---|---|
| | Zyg | 4-2C | 8C | 8C % | % Clv | C1 | C1– | C2 | Total Embs | Blast % | Hatch # | Hatch % |
| 0.25 mg/ml | 99 | 36 | 20 | 20.2 | 56.6 | 7 | 6 | 6 | 19 | 19.2 | 6 | 31.6 |
| 0.25 mg/ml | 99 | 17 | 46 | 46.5 | 63.6 | 5 | 7 | 8 | 20 | 20.2 | 9 | 45.0 |
| Total/Avg | 292 | 78 | 111 | 38.0 | (64.8) | 17 | 22 | 18 | 57 | (19.5) | 27 | (47.4) |
| 0.5 mg/ml | 100 | 40 | 34 | 34.0 | 74.0 | 4 | 6 | 1 | 11 | 11.0 | 5 | 45.5 |
| 0.5 mg/ml | 95 | 31 | 24 | 25.3 | 57.9 | 5 | 11 | 7 | 23 | 24.2 | 6 | 26.1 |
| 0.5 mg/ml | 99 | 15 | 46 | 46.5 | 61.6 | 8 | 5 | 5 | 18 | 18.2 | 9 | 50.0 |
| Total/Avg | 294 | 86 | 104 | 35.4 | (64.5) | 17 | 22 | 13 | 52 | (17.7) | 20 | (38.5) |

Example 6

Another experiment similar to Examples 4 and 5 was performed to test the reproducible effect of OSR treated sperm cells regarding a single bull by monitoring the development of embryos. Bull A (Holstein) was sampled three different times; Bull B was sampled five different times; Bull C only one time; all semen samples were subjected to standard sex sorting procedures using flow cytometry with vitamin B12 as the OSR at 0.25 mg/ml during the steps of staining, collection in the catch fluid and prior to cryopreservation (3 step). The control samples were not treated with vitamin B12. All experimental steps were done the same as in Example 4. The results are provided in Table 6, below.

TABLE 6

| | | | | | IVF (3 step) - Reproducibility | | | | | | | |
|---|---|---|---|---|---|---|---|---|---|---|---|---|
| | Zyg | 4-2C | 8C | 8C % | % Clv | C1 | C1– | C2 | Total Embs | Blast % | Freeze % | Hatch % |
| Bull A (Holstein) Trial 1 | | | | | | | | | | | | |
| Control | 507 | 85 | 119 | 23.5 | 40.2 | 34 | 19 | 31 | 84 | 16.6 | | 10.5 |
| 0.25 mg/ml | 434 | 92 | 100 | 23.0 | 44.2 | 27 | 14 | 44 | 85 | (19.6) | | 9.4 |
| Trial 2 | | | | | | | | | | | | |
| Control | 993 | 238 | 287 | 28.9 | 52.9 | 54 | 26 | 86 | 166 | 16.7 | | 8.1 |
| 0.25 mg/ml | 884 | 204 | 222 | 25.1 | 48.2 | 81 | 36 | 128 | 245 | (27.7) | | 13.2 |
| Trial 3 | | | | | | | | | | | | |
| Control | 907 | 209 | 215 | 23.7 | 46.7 | 70 | 27 | 90 | 187 | 20.6 | | 10.7 |
| 0.25 mg/ml | 1053 | 230 | 285 | 27.1 | 48.9 | 83 | 39 | 129 | 251 | (23.8) | | 11.6 |
| Average - Control | | | | | | | | | | (18.2) | | (9.6) |
| Average - 0.25 mg/ml | | | | | | | | | | (24.5) | | (11.8) |
| Bull B (Holstein) Trial 1 | | | | | | | | | | | | |
| Control | 507 | 85 | 119 | 23.5 | 40.2 | 34 | 19 | 31 | 84 | 16.6 | | 10.5 |
| 0.25 mg/ml | 434 | 92 | 100 | 23.0 | 44.2 | 27 | 14 | 44 | 85 | (19.6) | | 9.4 |
| Trial 2 | | | | | | | | | | | | |
| Control | 993 | 238 | 287 | 28.9 | 52.9 | 54 | 26 | 86 | 166 | 16.7 | | 8.1 |
| 0.25 mg/ml | 884 | 204 | 222 | 25.1 | 48.2 | 81 | 36 | 128 | 245 | (27.7) | | 13.2 |
| Trial 3 | | | | | | | | | | | | |
| Control | 907 | 209 | 215 | 23.7 | 46.7 | 70 | 27 | 90 | 187 | 20.6 | | 10.7 |
| 0.25 mg/ml | 1053 | 230 | 285 | 27.1 | 48.9 | 83 | 39 | 129 | 251 | (23.8) | | 11.6 |
| Trial 4 | | | | | | | | | | | | |
| Control | 550 | 122 | 177 | 32.2 | 54.4 | 12 | 19 | 56 | 87 | 15.8 | | 5.6 |
| 0.25 mg/ml | 595 | 124 | 183 | 30.8 | 51.6 | 12 | 8 | 52 | 72 | (12.1) | | 3.4 |
| Trial 5 | | | | | | | | | | | | |
| Control | 596 | 107 | 159 | 26.7 | 44.6 | 31 | 21 | 83 | 135 | 22.7 | | 8.7 |
| 0.25 mg/ml | 636 | 137 | 185 | 29.1 | 50.6 | 27 | 24 | 79 | 130 | (20.4) | | 8.0 |

TABLE 6-continued

IVF (3 step) - Reproducibility

| | Zyg | 4-2C | 8C | 8C % | % Clv | C1 | C1- | C2 | Total Embs | Blast % | Freeze % | Hatch % |
|---|---|---|---|---|---|---|---|---|---|---|---|---|
| Average - Control | | | | | | | | | | (18.5) | (8.8) | |
| Average - 0.25 mg/ml | | | | | | | | | | (21.7) | (9.7) | |
| Bull C | | | | | | | | | | | | |
| Trial 1 | | | | | | | | | | | | |
| Control | 454 | 113 | 265 | 58.4 | 83.3 | 21 | 17 | 49 | 87 | (19.2) | (8.4) | |
| 0.25 mg/ml | 509 | 104 | 335 | 65.8 | 86.2 | 31 | 27 | 62 | 120 | (23.6) | (11.4) | |

Example 7

A larger scale experiment was done to further test the reproducibility similar to what was done in Examples 6 and 7, but testing five bulls each three separate times. Semen samples from five bulls were sampled and sex sorted using flow cytometry in accordance with the earlier procedures and treated with 0.25 mg/ml vitamin B12 as the OSR (3 step). The control samples were not treated with vitamin B12.

TABLE 7

Averaged Effect (Holstein and Jersey Mix)

| | Zyg | 4-2C | 8C | 8C % | % Clv | C1 | C1- | C2 | Total Embs | Blast % | Hatch # | Hatch % |
|---|---|---|---|---|---|---|---|---|---|---|---|---|
| Control-A1 | 993 | 238 | 287 | 28.9 | 52.9 | 54 | 26 | 86 | 166 | 16.7 | | |
| Control-A2 | 507 | 85 | 119 | 23.5 | 40.2 | 34 | 19 | 31 | 84 | 16.6 | | |
| Control-A3 | 907 | 209 | 215 | 23.7 | 46.7 | 70 | 27 | 90 | 187 | 20.6 | | |
| Control-B1 | 96 | 36 | 8 | 8.3 | 45.8 | 1 | 0 | 5 | 6 | 6.3 | 2 | 33.3 |
| Control-B2 | 68 | 19 | 7 | 10.3 | 38.2 | 0 | 0 | 2 | 2 | 2.9 | 0 | 0.0 |
| Control-B3 | 91 | 31 | 19 | 20.9 | 54.9 | 2 | 3 | 10 | 15 | 16.5 | 5 | 33.3 |
| Control-C1 | 91 | 15 | 35 | 38.5 | 54.9 | 3 | 3 | 8 | 14 | 15.4 | 9 | 64.3 |
| Control-C2 | 90 | 25 | 29 | 32.2 | 60.0 | 4 | 5 | 9 | 18 | 20.0 | 10 | 55.6 |
| Control-C3 | 92 | 20 | 33 | 35.9 | 57.6 | 7 | 6 | 12 | 25 | 27.2 | 15 | 60.0 |
| Control-D1 | 97 | 39 | 39 | 40.2 | 80.4 | 5 | 5 | 3 | 13 | 13.4 | 7 | 53.8 |
| Control-D2 | 100 | 22 | 12 | 12.0 | 34.0 | 4 | 5 | | 9 | 9.0 | 2 | 22.2 |
| Control-D3 | 100 | 22 | 29 | 29.0 | 51.0 | 2 | 5 | 1 | 8 | 8.0 | 3 | 37.5 |
| Control-E1 | 91 | 25 | 35 | 38.5 | 65.9 | 3 | 2 | 4 | 9 | 9.9 | 3 | 33.3 |
| Control-E2 | 93 | 40 | 19 | 20.4 | 63.4 | | 1 | 2 | 3 | 3.2 | 0 | 0.0 |
| Control-E3 | 98 | 25 | 25 | 25.5 | 51.0 | 3 | 6 | 5 | 14 | 14.3 | 6 | 42.9 |
| Total/Avg | 3514 | 851 | 911 | 25.9 | (50.1) | 192 | 113 | 268 | 573 | (16.3) | 62 | (10.8) |
| 0.25 -A1 | 884 | 204 | 222 | 25.1 | 48.2 | 81 | 36 | 128 | 245 | 27.7 | | |
| 0.25 -A2 | 434 | 92 | 100 | 23.0 | 44.2 | 27 | 14 | 44 | 85 | 19.6 | | |
| 0.25 -A3 | 1053 | 230 | 285 | 27.1 | 48.9 | 83 | 39 | 129 | 251 | 23.8 | | |
| 0.25 -B1 | 91 | 33 | 6 | 6.6 | 42.9 | 0 | 2 | 3 | 5 | 5.5 | 2 | 40.0 |
| 0.25 -B2 | 93 | 38 | 20 | 21.5 | 62.4 | 4 | 2 | 10 | 16 | 17.2 | 10 | 62.5 |
| 0.25 -B3 | 91 | 26 | 16 | 17.6 | 46.2 | 2 | 3 | 10 | 15 | 16.5 | 6 | 40.0 |
| 0.25 -C1 | 92 | 24 | 34 | 37.0 | 63.0 | 5 | 3 | 11 | 19 | 20.7 | 14 | 73.7 |
| 0.25 -C2 | 96 | 31 | 23 | 24.0 | 56.3 | 1 | 3 | 3 | 7 | 7.3 | 5 | 71.4 |
| 0.25 -C3 | | | | | | | | | | | | |
| 0.25 -D1 | 94 | 25 | 45 | 47.9 | 74.5 | 5 | 9 | 4 | 18 | 19.1 | 12 | 66.7 |
| 0.25 -D2 | 99 | 36 | 20 | 20.2 | 56.6 | 7 | 6 | 6 | 19 | 19.2 | 6 | 31.6 |
| 0.25 -D3 | 99 | 17 | 46 | 46.5 | 63.6 | 5 | 7 | 8 | 20 | 20.2 | 9 | 45.0 |
| 0.25 -E1 | 97 | 25 | 39 | 40.2 | 66.0 | 6 | 9 | 5 | 20 | 20.6 | 8 | 40.0 |
| 0.25 -E2 | 97 | 34 | 30 | 30.9 | 66.0 | 5 | 6 | 5 | 16 | 16.5 | 4 | 25.0 |
| 0.25 -E3 | 97 | 23 | 33 | 34.0 | 57.7 | 6 | 7 | 6 | 19 | 19.6 | 9 | 47.4 |
| Total/Avg | 3417 | 838 | 919 | 26.9 | (51.4) | 237 | 146 | 372 | 755 | (22.1) | 85 | (11.3) |

Example 8

In an additional experiment, post-thaw motility and progressive motility were checked using CASA at 0, 3 and 5 hours after thawing sex sorted semen samples (sorted using flow cytometry) treated with vitamin B12 as the antioxidant. The OSR was not added to the control samples. The semen samples were derived from two Holstein bulls. 0.25 mg/ml concentration of vitamin B12 was added to the test samples during the staining step, the collecting step (in the catch fluid of the collecting vessel) and in the cryoprotectant extender prior to freezing the sample (3 step). The results are shown in Table 8 below.

TABLE 8

| | Post-Thaw Motility (3 step) | | | | | | | | | | |
|---|---|---|---|---|---|---|---|---|---|---|---|
| | Total cells | Motile (%) | Prog Mot (%) | VAP (µm/s) | VSL (µm/s) | VCL (µm/s) | ALH (µm) | BCF (Hz) | STR (%) | LIN (%) | PIA (%) |
| Bull A | | | | | | | | | | | |
| 0 hr Post-Thaw: | | | | | | | | | | | |
| Bull A - Control | 1884 | 77 | 53 | 107 | 81 | 211 | 9 | 23 | 76 | 40 | |
| Bull A - Control | 1275 | 74 | 51 | 99 | 75 | 198 | 9 | 24 | 77 | 41 | 90 |
| Average | | (76) | (52) | 103 | 78 | 205 | 9 | 24 | 77 | 41 | |
| Bull A - 0.25 | 1074 | 73 | 51 | 89 | 68 | 183 | 8 | 26 | 77 | 40 | |
| Bull A - 0.25 | 1519 | 69 | 50 | 101 | 78 | 195 | 8 | 27 | 78 | 43 | 90 |
| Average | | (71) | (51) | 95 | 73 | 189 | 8 | 27 | 78 | 42 | |
| 3 hr Post-Thaw: | | | | | | | | | | | |
| Bull A - Control | 1064 | 48 | 3 | 38 | 29 | 76 | 6 | 14 | 77 | 40 | 56 |
| Bull A - Control | 683 | 53 | 7 | 44 | 36 | 80 | 5 | 17 | 84 | 46 | 63 |
| Average | | (50) | (5) | 41 | 32.5 | 78 | 5.5 | 15.5 | 80.5 | 43 | 59.5 |
| Bull A - 0.25 | 870 | 64 | 22 | 48 | 39 | 84 | 8 | 14 | 77 | 41 | 86 |
| Bull A - 0.25 | 978 | 46 | 7 | 41 | 31 | 83 | 8 | 14 | 77 | 38 | 76 |
| Average | | (55) | (15) | 45 | 35 | 84 | 8 | 14 | 77 | 40 | 81 |
| 5 hr Post-Thaw: | | | | | | | | | | | |
| Bull A - Control | 903 | 40 | 8 | 14 | 11 | 25 | 3 | 7 | 14 | 9 | 52 |
| Bull A - Control | 517 | 15 | 1 | 12 | 10 | 18 | 2 | 10 | 17 | 18 | 60 |
| Average | | (27.5) | (4.5) | 13 | 10.5 | 21.5 | 2.5 | 8.5 | 15.5 | 13.5 | 56 |
| Bull A - 0.25 | 708 | 61 | 26 | 17 | 17 | 23 | 2 | 6 | 13 | 12 | 79 |
| Bull A - 0.25 | 747 | 34 | 7 | 20 | 16 | 28 | 3 | 8 | 14 | 13 | 72 |
| Average | | (47.5) | (16.5) | 18.5 | 16.5 | 25.5 | 2.5 | 7 | 13.5 | 12.5 | 75.5 |
| Bull B | | | | | | | | | | | |
| 0 hr Post-Thaw: | | | | | | | | | | | |
| Bull B - Control | 1878 | 73 | 57 | 88 | 73 | 153 | 7 | 27 | 83 | 49 | |
| Bull B - Control | 1706 | 72 | 54 | 83 | 69 | 142 | 6 | 28 | 84 | 51 | 90 |
| Average | | (73) | (55.5) | 85.5 | 71 | 148 | 7 | 28 | 84 | 50 | |
| Bull B - 0.25 | 1804 | 79 | 58 | 85 | 70 | 145 | 6 | 28 | 83 | 51 | |
| Bull B - 0.25 | 1150 | 79 | 54 | 81 | 67 | 143 | 6 | 29 | 84 | 51 | 90 |
| Average | | (79) | (56) | 83 | 69 | 144 | 6 | 29 | 84 | 51 | |
| 3 hr Post-Thaw: | | | | | | | | | | | |
| Bull B - Control | 666 | 30 | 10 | 39 | 25 | 80 | 8 | 16 | 66 | 33 | 60 |
| Bull B - Control | 670 | 50 | 12 | 45 | 37 | 85 | 6 | 16 | 82 | 44 | 72 |
| Average | | (50) | (11) | 42 | 31 | 82.5 | 7 | 16 | 74 | 38.5 | 66 |
| Bull B - 0.25 | 928 | 56 | 18 | 50 | 39 | 96 | 6 | 18 | 80 | 42 | 83 |
| Bull B - 0.25 | 772 | 42 | 12 | 46 | 37 | 89 | 6 | 18 | 80 | 42 | 82 |
| Average | | (49) | (15) | 48 | 38 | 93 | 6 | 18 | 80 | 42 | 82.5 |
| 5 hr Post-Thaw: | | | | | | | | | | | |
| Bull B - Control | 539 | 0 | 0 | 40 | 16 | 52 | 0 | 26 | 40 | 31 | 46 |
| Bull B - Control | 609 | 0 | 0 | 35 | 26 | 44 | 0 | 71 | 75 | 39 | 61 |
| Average | | (0) | (0) | 37.5 | 21 | 48 | 0 | 48.5 | 57.5 | 35 | 53.5 |
| Bull B - 0.25 | 902 | 43 | 4 | 41 | 28 | 85 | 7 | 14 | 70 | 34 | 83 |
| Bull B - 0.25 | 721 | 21 | 0 | 38 | 21 | 70 | 4 | 14 | 57 | 32 | 73 |
| Average | | (32) | (2) | 39.5 | 24.5 | 77.5 | 5.5 | 14 | 63.5 | 33 | 78 |

Example 9

In an additional experiment, motility and progressive motility were checked at 0 hours and 3 hours after thawing sex sorted semen samples (sorted using flow cytometry) treated with the antioxidant, vitamin B12. The OSR was not added to the control sample. The semen samples were derived from two different breeds of bull, one a Holstein the other Texas Longhorn. 0.25 mg/ml concentration of vitamin B12 was added to the test samples either (i) during the staining step (1 step-stain); (ii) the staining step and the collecting step (in the catch fluid of the collecting vessel) (2 step-stain); (iii) in the staining step, the collecting step and the freezing step (in the cryoprotectant extender prior to freezing the sample) (3 step)—Table 9 (A) for 3 hr, and (B) for 0 hr; or (iv) only prior to the cryopreservation step (1 step-freeze)—Table 9 (C) for 3 hr.

TABLE 9 (A)

3 hr Post-Thaw Motility (3 step; 2 step-stain; 1 step-stain)

|  | Total cells | Motile (%) | Prog Mot (%) | VAP (µm/s) | VSL (µm/s) | VCL (µm/s) | ALH (µm) | BCF (Hz) | STR (%) | LIN (%) | PIA (%) |
|---|---|---|---|---|---|---|---|---|---|---|---|
| Bull 1 (TL) 3 hr Post-Thaw |  |  |  |  |  |  |  |  |  |  |  |
| Control |  | (12) | (3) | 42 | 35 | 77 | 3 | 19 | 83 | 46 | 23 |
| 3 step (+ + +) |  | 42 | 25 | 55 | 47 | 101 | 5 | 23 | 84 | 48 | 73 |
| 2 step-stain (+ + −) |  | 25 | 9 | 47 | 41 | 85 | 5 | 21 | 87 | 49 | 47 |
| 1 step-stain (+ − −) |  | 37 | 23 | 56 | 47 | 84 | 5 | 16 | 85 | 57 | 52 |
| Bull 2 (Jersey) 3 hr Post-Thaw |  |  |  |  |  |  |  |  |  |  |  |
| Control |  | (72) | (63) | 70 | 59 | 108 | 5 | 19 | 85 | 56 | 72 |
| 3 step (+ + +) |  | 75 | 70 | 81 | 74 | 124 | 5 | 22 | 88 | 58 | 80 |
| 2 step-stain (+ + −) |  | 57 | 35 | 60 | 50 | 105 | 5 | 19 | 84 | 48 | 78 |
| 1 step-stain (+ − −) |  | 47 | 32 | 59 | 49 | 98 | 5 | 19 | 84 | 51 | 71 |
| Average |  |  |  |  |  |  |  |  |  |  |  |
| Avg - Control |  | (42) | (33) | 56 | 47 | 92 | 4 | 19 | 84 | 51 | 48 |
| 3 step (+ + +) |  | 58 | 47 | 68 | 60 | 112 | 5 | 23 | 86 | 53 | 77 |
| 2 step-stain (+ + −) |  | 41 | 22 | 53 | 45 | 95 | 5 | 20 | 85 | 48 | 63 |
| 1 step-stain (+ − −) |  | 42 | 28 | 57 | 48 | 91 | 5 | 18 | 85 | 54 | 61 |

TABLE 9 (B)

0 hr Post-Thaw Motility (3 step; 2 step-stain; 1 step-stain)

|  | Total cells | Motile (%) | Prog Mot (%) | VAP (µm/s) | VSL (µm/s) | VCL (µm/s) | ALH (µm) | BCF (Hz) | STR (%) | LIN (%) | PIA (%) |
|---|---|---|---|---|---|---|---|---|---|---|---|
| Bull 1 (TL) 0 hr Post-Thaw |  |  |  |  |  |  |  |  |  |  |  |
| Control |  | (58.5) | (49.5) | 93.5 | 81.0 | 161.5 | 7.0 | 26.0 | 86.5 | 52.5 |  |
| 3 step (+ + +) |  | 76 | 60 | 89.5 | 79.5 | 154.5 | 7.0 | 27.5 | 89.0 | 56.5 |  |
| 2 step-stain (+ + −) |  | 57 | 48 | 96.0 | 84.0 | 168.0 | 7.0 | 25.5 | 87.5 | 52.0 |  |
| 1 step-stain (+ − −) |  | 60.5 | 55 | 95.0 | 83.5 | 167.0 | 7.0 | 26.5 | 88.5 | 52.0 |  |
| Bull 2 (Jersey) 0 hr Post-Thaw |  |  |  |  |  |  |  |  |  |  |  |
| Control |  | (79) | (68) | 105.0 | 89.0 | 179.0 | 7.0 | 26.0 | 86.0 | 53.0 |  |
| 3 step (+ + +) |  | 70 | 57.7 | 94.5 | 82.0 | 165.5 | 6.5 | 30.0 | 86.5 | 52.0 |  |
| 2 step-stain (+ + −) |  | 74 | 67 | 97.0 | 85.0 | 170.0 | 7.0 | 27.0 | 88.0 | 52.0 |  |
| 1 step-stain (+ − −) |  | 80 | 71 | 104.0 | 88.0 | 189.0 | 8.0 | 26.0 | 85.0 | 49.0 |  |

TABLE 9 (C)

3 hr Post-Thaw Motility (1 step-freeze)

| Bull 3 3 hr Post-Thaw | Total Cells | Motile (%) | Prog Mot (%) | VAP (µm/s) | VSL (µm/s) | VCL (µm/s) | ALH (µm) | BCF (Hz) | STR (%) | LIN (%) | PIA (%) |
|---|---|---|---|---|---|---|---|---|---|---|---|
| Control | 418 | 20 | 0 | 38 | 26 | 67 | 14 | 12 |  |  | 63 |
| Control | 238 | 29 | 0 | 35 | 23 | 53 | 0 | 14 |  |  | 59 |
| Avg - Control | 656 | (24.5) | (0) | 36.5 | 24.5 | 60 | 7 | 13 |  |  | 61 |
| 1 step-freeze (− − +) | 384 | 50 | 10 | 43 | 35 | 80 | 5 | 17 |  |  | 63 |
| 1 step-freeze (− − +) | 385 | 59 | 17 | 48 | 40 | 86 | 5 | 19 |  |  | 83 |
| 1 step-freeze (− − +) | 210 | 32 | 4 | 41 | 31 | 75 | 6 | 13 |  |  | 67 |
| 1 step-freeze (− − +) | 301 | 45 | 11 | 45 | 33 | 81 | 6 | 13 |  |  | 85 |
| Avg - 1 step-frz | 1280 | (46.5) | (10.5) | 44.25 | 34.75 | 80.5 | 5.5 | 15.5 |  |  | 74.5 |

Example 10

An additional experiment was conducted to assess the pregnancy rate of female bovines inseminated with sorted sperm cell samples treated with an antioxidant. Semen samples from two bulls were sex sorted using the protocol described above. 0.25 mg/ml concentration of vitamin B12 was added to the test samples during the staining step, the collecting step (in the catch fluid of the collecting vessel) and the freezing step (3 step).

Frozen semen straws containing sex sorted sperm cell samples were thawed using standard procedures. An artificial insemination (AI) gun was warmed as needed to approach body temperature of the recipient, and a straw was placed in the barrel of the insemination gun. The sealed end of the straw was cut off and a plastic sheath was placed over the straw and gun for hygienic purposes. The female was previously placed in a restraining shoot for insemination. The gun was threaded through the vagina and cervix and semen distributed in the uterine body. 384 females were inseminated, each inseminated with a single sperm cell dose, and each dose containing 2.1 million sperm cells in 0.25 ml. Pregnancy checks were made 33-40 days post insemination with an ultrasound machine. The results are shown in Table 10 below.

TABLE 10

| | Pregnancies (3 step) | | |
|---|---|---|---|
| | | Inseminations | Percent Pregnancy |
| Bull A | Control | 87 | 32.8 |
| | 0.25 mg/ml | 100 | 35.6 |
| Bull B | Control | 99 | 30.9 |
| | 0.25 mg/ml | 98 | 27.0 |
| Total/Average | Control | 186 | (31.9) |
| Total/Average | 0.25 mg/ml | 198 | (31.3) |

Example 11

Additional pregnancy field trials were performed using the sex-sorted semen treated with vitamin B12 at 0.25 mg/ml added to the test samples during the staining step, the collecting step and again in the freezing step (3-step), as done in Example 10 was evaluated another time looking using semen from five different Holstein bulls. Each semen sample was split into control and vitamin B12 (0.25 mg/ml) treatment groups, and later inseminated into primiparous recipient heifers. Pregnancy checks were made 33-40 days post insemination using ultrasound. The results are shows in Table 11 below.

TABLE 11

| | Pregnancies (3 step) | | |
|---|---|---|---|
| | Antioxidant | Inseminations | Percent Pregnancy |
| Bull A | Control | | 27.9 |
| | 0.25 mg/ml | | 28.4 |
| Bull B | Control | | 26.1 |
| | 0.25 mg/ml | | 28.0 |
| Bull C | Control | | 32.8 |
| | 0.25 mg/ml | | 35.6 |
| Bull D | Control | | 26.0 |
| | 0.25 mg/ml | | 30.7 |
| Bull E | Control | | 50.0 |
| | 0.25 mg/ml | | 57.0 |
| Total/Average | Control | 499 | (32.6) |
| Total/Average | 0.25 mg/ml | 374 | (35.9) |

Example 12

The levels of DNA fragmentation were also screened using a DNA fragmentation 'Halomax for animals' kit (Halotech DNA, sl, Madrid, Spain) to determine if there were any advantageous effects of using the antioxidants during the staining and processing of sex-sorted sperm. Two different breeds of cattle, Jersey and Holstein, were examined using two different concentrations of antioxidant, 0.25 mg/ml and 0.5 mg/ml of vitamin B12 with the 3 step protocol adding the same concentration of OSR during cell staining, in the collection catch fluid and prior to cryopreservation. One of the bulls was used to evaluate the effect of addition or omission of OSR at one or more of the sperm sorting steps. Motility and the level of DNA fragmentation were both recorded. The results are shown in Table 12 below.

TABLE 12

| DNA Fragmentation (1 step-stain, 2 step, 3 step) | | | | | |
|---|---|---|---|---|---|
| | % Motility | | % DNA Fragmentation | | |
| | 0 hr | 3 hr | 0 hr | 24 hr | 48 hr |
| Bull A (Jersey) | | | | | |
| Control | 57 | 17 | 1 | 1 | 1.7 |
| 0.25 mg/ml | 72 | 51 | 0.3 | 0.3 | 0.7 |
| 0.5 mg/ml | 60 | 42 | 0.3 | 0.7 | 1.3 |
| Bull B (Holstein) | | | | | |
| Control | 62 | 32 | 0.3 | 0.3 | 0.7 |
| 0.25 mg/ml | 67 | 32 | 0 | 0.3 | 0.3 |
| 0.5 mg/ml | 79 | 48 | 0.3 | 0.3 | 0.7 |
| Bull C (Jersey) Trial 1 | | | | | |
| Control | 79 | 72 | 1 | 1 | 1 |
| 3 step (+++) | 70 | 75 | 0 | 0.3 | 0.3 |
| 2 step-stain (++−) | 74 | 57 | 0.3 | 1 | 1 |
| 1 step-stain (+−−) | 80 | 47 | 0.7 | 1 | 1.3 |
| Trial 2 | | | | | |
| Control | 59 | 12 | 0.3 | 1.7 | 1.7 |
| 3 step (+++) | 76 | 42 | 0.3 | 0.3 | 0.7 |
| 2 step-stain (++−) | 57 | 25 | 0.3 | 0.7 | 0.7 |
| 1 step-stain (+−−) | 61 | 37 | 0.7 | 1 | 1 |

Example 13

The effect of OSR on motility was evaluated as a function of the concentration of the sex-sorted sperm in the frozen straw. Tests were performed using vitamin B12 as the OSR at three different concentrations of the antioxidant: 0.15 mg/ml; 0.25 mg/ml and 0.35 mg/ml; all were added to the test samples during the staining step, the collecting step and again in the freezing step (3-step), as done in Example 8. Holstein sperm was evaluated at three sperm cell concentrations based upon total number of sperm per straw: 1 million sperm/straw; 2.1 million sperm/straw; and 5 million sperm/straw. Motility was recorded 3 hr post-thaw.

A Jersey sperm sample was also evaluated in the same manner using 0.15 mg/ml or 0.25 mg/ml vitamin B12 at each of the three stages (3 step), but only at the 2.1 million sperm/straw concentration. The results are shown in Table 13.

TABLE 13

Frozen Sperm Cell Concentration (3 step)

| | Motile | Prog | VAP | VSL | VCL | ALH | BCF | STR | LIN | PIA |
|---|---|---|---|---|---|---|---|---|---|---|
| (Holstein) 1M/straw | | | | | | | | | | |
| Control | 20 | 4 | 40 | 32 | 76 | 3 | 15 | 78 | 42 | 43 |
| .15 mg/ml | 48 | 18 | 48 | 42 | 81 | 4 | 12 | 88 | 53 | 66 |
| .25 mg/ml | 48 | 29 | 55 | 47 | 92 | 4 | 22 | 87 | 53 | 58 |
| .35 mg/ml | 65 | 46 | 58 | 51 | 94 | 4 | 23 | 88 | 55 | 70 |
| 2.1M/straw | | | | | | | | | | |
| Control | 28 | 2 | 39 | 33 | 73 | 6 | 16 | 85 | 46 | 41 |
| .15 mg/ml | 49 | 10 | 44 | 38 | 79 | 5 | 18 | 86 | 48 | 72 |
| .25 mg/ml | 48 | 18 | 46 | 40 | 81 | 5 | 20 | 87 | 50 | 76 |
| .35 mg/ml | 46 | 30 | 58 | 51 | 99 | 5 | 23 | 88 | 53 | 60 |
| 5M/straw | | | | | | | | | | |
| Control | 20 | 1 | 39 | 29 | 69 | 7 | 13 | 74 | 43 | 46 |
| .25 mg/ml | 24 | 2 | 41 | 28 | 69 | 7 | 14 | 70 | 42 | 68 |
| .35 mg/ml | 28 | 3 | 41 | 32 | 68 | 7 | 14 | 69 | 43 | 69 |
| .5 mg/ml | 14 | 3 | 43 | 30 | 71 | 6 | 15 | 70 | 43 | 50 |
| (Jersey) 2.1M/straw | | | | | | | | | | |
| Control | 25 | 2 | 37 | 28 | 55 | 2 | 11 | 76 | 52 | 53 |
| .15 mg/ml | 25 | 4 | 42 | 35 | 75 | 6 | 15 | 84 | 47 | 63 |
| .25 mg/ml | 48 | 20 | 51 | 43 | 87 | 5 | 20 | 85 | 50 | 78 |

Example 14

The effect of a different OSR on bovine sperm motility was evaluated after zero hour and a three hour post-thaw period. The OSR, α-tocopheryl, a form of Vitamin E, was purchased as 'polyoxyethanyl-α-tocopheryl sebacate' in a 15% stock solution (Aldrich). Tests were performed using α-tocopheryl as the OSR, at three different concentrations: 0.01 mg/ml; 0.1 mg/ml and 0.5 mg/ml; all were added to the test samples during the staining step, the collecting step and again in the freezing step (3-step), as done in the prior Examples. Sex-sorted Holstein sperm was evaluated using a standard sperm concentration of 2.1 million sperm/straw processed from three separate bulls. Motility of the treated samples were compared to untreated controls and recorded at 0 hr and 3 hr post-thaw.

TABLE 14

Motility with α-tocopheryl (vitamin E) (3 step)

| | Total cells | Motile | Prog | VAP | VSL | VCL | ALH | BCF | STR | LIN |
|---|---|---|---|---|---|---|---|---|---|---|
| Holstein 0 hr Post-Thaw | | | | | | | | | | |
| Bull A | | | | | | | | | | |
| Control | 548 | 56 | 25 | 75 | 52 | 151 | 7 | 22 | 74 | 39 |
| 0.01 | 617 | 72 | 17 | 100 | 49 | 201 | 10 | 20 | 56 | 27 |
| 0.1 | 458 | 73 | 33 | 99 | 62 | 217 | 9 | 22 | 66 | 32 |
| 0.5 | 424 | 63 | 36 | 97 | 68 | 214 | 9 | 22 | 72 | 34 |
| Bull B | | | | | | | | | | |
| Control | 548 | 56 | 25 | 75 | 52 | 151 | 7 | 22 | 74 | 39 |
| 0.01 | 617 | 72 | 17 | 100 | 49 | 201 | 10 | 20 | 56 | 27 |
| 0.1 | 458 | 73 | 33 | 99 | 62 | 217 | 9 | 22 | 66 | 32 |
| 0.5 | 424 | 63 | 36 | 97 | 68 | 214 | 9 | 22 | 72 | 34 |
| Bull C (1) | | | | | | | | | | |
| Control | 280 | 50 | 30 | 66 | 51 | 140 | 7 | 20 | 78 | 39 |
| 0.01 | 530 | 59 | 39 | 89 | 68 | 188 | 10 | 20 | 76 | 38 |
| 0.1 | 518 | 63 | 35 | 86 | 61 | 196 | 10 | 20 | 72 | 33 |
| 0.5 | 269 | 30 | 17 | 75 | 53 | 179 | 8 | 22 | 72 | 31 |

TABLE 14-continued

Motility with α-tocopheryl (vitamin E) (3 step)

|   | Total cells | Motile | Prog | VAP | VSL | VCL | ALH | BCF | STR | LIN |
|---|---|---|---|---|---|---|---|---|---|---|
| Bull C (2) | | | | | | | | | | |
| Control | 364 | 23 | 12 | 65 | 54 | 116 | 5 | 25 | 82 | 49 |
| 0.01 | 347 | 36 | 27 | 86 | 78 | 140 | 6 | 26 | 90 | 57 |
| 0.1 | 822 | 27 | 18 | 84 | 75 | 149 | 6 | 25 | 88 | 52 |
| 0.5 | 764 | 29 | 18 | 74 | 64 | 130 | 7 | 28 | 87 | 55 |

Holstein 3 hr Post-Thaw

|   | Total cells | Motile | Prog | VAP | VSL | VCL | ALH | BCF | STR | LIN |
|---|---|---|---|---|---|---|---|---|---|---|
| A-toc Bull A | | | | | | | | | | |
| Control | 260 | 25 | 6 | 39 | 33 | 71 | 5 | 16 | 83 | 47 |
| 0.01 | 253 | 64 | 20 | 51 | 42 | 92 | 5 | 21 | 84 | 49 |
| 0.1 | 297 | 62 | 32 | 54 | 46 | 101 | 5 | 22 | 86 | 48 |
| 0.5 | 235 | 54 | 29 | 60 | 51 | 106 | 5 | 24 | 85 | 49 |
| Bull B | | | | | | | | | | |
| Control | 309 | 29 | 8 | 46 | 37 | 83 | 6 | 19 | 82 | 46 |
| 0.01 | 126 | 28 | 9 | 54 | 39 | 103 | 4 | 21 | 76 | 41 |
| 0.1 | 154 | 14 | 4 | 56 | 36 | 100 | 6 | 18 | 73 | 38 |
| 0.5 | 151 | 36 | 10 | 57 | 41 | 104 | 5 | 22 | 77 | 44 |
| Bull C (1) | | | | | | | | | | |
| Control | 200 | 14 | 2 | 40 | 33 | 77 | 5 | 18 | 83 | 44 |
| 0.01 | 222 | 19 | 3 | 41 | 38 | 60 | 4 | 29 | 93 | 70 |
| 0.1 | 155 | 15 | 5 | 49 | 41 | 94 | 7 | 21 | 84 | 45 |
| 0.5 | 82 | 26 | 13 | 50 | 44 | 89 | 5 | 18 | 87 | 50 |
| Bull C (2) | | | | | | | | | | |
| Control | 207 | 2 | 0 | 19 | 15 | 26 | 1 | 11 | 73 | 27 |
| 0.01 | 270 | 6 | 0 | 35 | 21 | 55 | 0 | 13 | 60 | 39 |
| 0.1 | 658 | 4 | 0 | 38 | 29 | 63 | 1 | 8 | 76 | 46 |
| 0.5 | 278 | 2 | 0 | 37 | 21 | 64 | 0 | 14 | 55 | 33 |

Example 15

The effect of a third OSR on bovine sperm motility was evaluated after zero hour, three hour and six hour post-thaw periods. Alpha-ketoglutarate (AKG) was freshly made and used at three different concentrations: 0.25 mg/ml; 0.35 mg/ml and 0.45 mg/ml; all were added to the test samples during the staining step, the collecting step and again in the freezing step (3-step), as done in the prior Examples. Sex-sorted Holstein and Jersey bovine sperm were evaluated using a standard concentration of 2.1 M sperm/straw. Motility of the treated samples was compared to untreated controls at 0 hr, 3 hr and 6 hr post-thaw.

TABLE 15

Alpha-keto Glutarate (AKG) (3 step)

|   | Motile | Prog | VAP | VSL | VCL | ALH | BCF | STR | LIN | PIA |
|---|---|---|---|---|---|---|---|---|---|---|
| Holstein - 0 hr | | | | | | | | | | |
| control | 41 | 16 | 69 | 44 | 143 | 8 | 21 | 66 | 34 | |
| .25 mg/ml | 91 | 75 | 104 | 81 | 185 | 8 | 27 | 82 | 48 | |
| .35 mg/ml | 80 | 65 | 94 | 80 | 165 | 7 | 29 | 85 | 51 | |
| .45 mg/ml | 86 | 75 | 98 | 88 | 162 | 7 | 30 | 89 | 57 | |
| Holstein - 3 hr | | | | | | | | | | |
| control | 4 | 0 | 36 | 24 | 53 | 0 | 10 | 67 | 48 | 44 |
| .25 mg/ml | 77 | 60 | 99 | 79 | 176 | 7 | 26 | 81 | 45 | 89 |
| .35 mg/ml | 63 | 48 | 85 | 70 | 145 | 6 | 25 | 83 | 50 | 80 |
| .45 mg/ml | 60 | 56 | 94 | 80 | 145 | 5 | 24 | 85 | 56 | 80 |
| control | 30 | 7 | 40 | 30 | 68 | 3 | 13 | 74 | 46 | 44 |
| .25 mg/ml | 71 | 55 | 96 | 77 | 169 | 6 | 26 | 81 | 47 | 89 |
| .35 mg/ml | 64 | 38 | 69 | 57 | 117 | 5 | 21 | 84 | 50 | 80 |
| .45 mg/ml | 60 | 50 | 90 | 75 | 144 | 6 | 25 | 84 | 53 | 80 |
| Holstein - 6 hr | | | | | | | | | | |
| control | 4 | 0 | 38 | 23 | 55 | 0 | 12 | 61 | 42 | 56 |
| .25 mg/ml | 36 | 7 | 44 | 33 | 87 | 6 | 17 | 76 | 39 | 73 |

TABLE 15-continued

| Alpha-keto Glutarate (AKG) (3 step) | | | | | | | | | | |
|---|---|---|---|---|---|---|---|---|---|---|
| | Motile | Prog | VAP | VSL | VCL | ALH | BCF | STR | LIN | PIA |
| .35 mg/ml | 58 | 7 | 42 | 32 | 80 | 7 | 16 | 76 | 40 | 85 |
| .45 mg/ml | 52 | 22 | 55 | 46 | 96 | 5 | 22 | 82 | 48 | 79 |
| control | 4 | 0 | 38 | 23 | 55 | 0 | 12 | 61 | 42 | 56 |
| .25 mg/ml | 36 | 7 | 44 | 33 | 87 | 6 | 17 | 76 | 39 | 73 |
| .35 mg/ml | 58 | 7 | 42 | 32 | 80 | 7 | 16 | 76 | 40 | 85 |
| .45 mg/ml | 52 | 22 | 55 | 46 | 96 | 5 | 22 | 82 | 48 | 79 |
| Jersey - 0 hr | | | | | | | | | | |
| control | 72 | 60 | 82 | 72 | 141 | 6 | 25 | 87 | 53 | |
| .25 mg/ml | 67 | 51 | 83 | 68 | 152 | 7 | 24 | 83 | 48 | |
| .35 mg/ml | 57 | 43 | 79 | 63 | 146 | 6 | 25 | 82 | 47 | |
| .45 mg/ml | 81 | 66 | 81 | 70 | 133 | 6 | 27 | 87 | 56 | |
| Jersey - 3 hr | | | | | | | | | | |
| control | 13 | 1 | 36 | 24 | 65 | 2 | 14 | 66 | 38 | 42 |
| .25 mg/ml | 33 | 16 | 65 | 49 | 117 | 5 | 24 | 79 | 46 | 62 |
| .35 mg/ml | 26 | 10 | 59 | 46 | 110 | 6 | 25 | 80 | 45 | 54 |
| .45 mg/ml | 59 | 25 | 67 | 50 | 66 | 6 | 25 | 78 | 45 | 71 |

Example 16

The effect of combining two antioxidants on bovine sperm motility was evaluated after zero hour, three hour and six hour post-thaw periods. Vitamin B12 was used at 0.25 mg/ml and fresh alpha-ketoglutarate (AKG) was used at 0.35 mg/ml. Either vitamin B12 or AKG or both treatments were added at the designated concentrations during the staining step, the collecting step and again in the freezing step (3-step), as done earlier. Sex-sorted sperm from three Jersey bulls were evaluated using standard 2.1 M sperm/straw. Motility of the treated samples was compared to untreated controls at 0 hr, 3 hr and 6 hr post-thaw.

TABLE 16

| Combination AKG, Vitamin B12, and Combination (3 step) | | | | | | | | | |
|---|---|---|---|---|---|---|---|---|---|
| | Motile | PROG | VAP | VSL | VCL | ALH | BCF | STR | LIN |
| Jersey 1 - 0 hr | | | | | | | | | |
| Control | 75 | 67 | 99 | 87 | 162 | 6 | 30 | 88 | 56 |
| B12 - 0.25 mg/ml | 88 | 78 | 97 | 87 | 157 | 6 | 33 | 89 | 58 |
| AKG - 0.35 mg/ml | 87 | 75 | 93 | 81 | 148 | 6 | 31 | 88 | 57 |
| COMBO | 78 | 69 | 93 | 83 | 149 | 6 | 32 | 89 | 57 |
| Jersey 1 - 3 hr | | | | | | | | | |
| Control | 43 | 5 | 41 | 33 | 74 | 6 | 15 | 56 | 46 |
| B12 - 0.25 mg/ml | 53 | 34 | 58 | 51 | 93 | 4 | 23 | 87 | 55 |
| AKG - 0.35 mg/ml | 60 | 44 | 82 | 67 | 136 | 5 | 27 | 83 | 50 |
| COMBO | 51 | 36 | 79 | 63 | 129 | 5 | 25 | 80 | 50 |
| Jersey 1 - 6 hr | | | | | | | | | |
| Control | 2 | 1 | 48 | 38 | 58 | 3 | 8 | 75 | 64 |
| B12 - 0.25 mg/ml | 37 | 2 | 38 | 28 | 61 | 4 | 15 | 73 | 48 |
| AKG - 0.35 mg/ml | 36 | 18 | 50 | 42 | 90 | 4 | 22 | 82 | 46 |
| COMBO | 35 | 6 | 45 | 34 | 81 | 5 | 17 | 76 | 43 |
| Jersey 2 - 3 hr | | | | | | | | | |
| Control | 18 | 1 | 35 | 22 | 57 | 5 | 13 | 61 | 38 |
| B12 - 0.25 mg/ml | 66 | 30 | 51 | 43 | 93 | 5 | 18 | 84 | 47 |
| AKG - 0.35 mg/ml | 64 | 50 | 78 | 62 | 117 | 5 | 19 | 82 | 56 |
| COMBO | 50 | 38 | 72 | 57 | 124 | 5 | 24 | 80 | 48 |
| Jersey 2 - 6 hr | | | | | | | | | |
| Control | 1 | 0 | 16 | 16 | 35 | 0 | 0 | 50 | 23 |
| B12 - 0.25 mg/ml | 24 | 1 | 36 | 24 | 51 | 1 | 17 | 65 | 47 |
| AKG - 0.35 mg/ml | 44 | 5 | 42 | 36 | 68 | 2 | 17 | 86 | 54 |
| COMBO | 46 | 18 | 61 | 46 | 111 | 5 | 21 | 77 | 44 |
| Jersey 3 - 0 hr | | | | | | | | | |
| Control | 80 | 60 | 100 | 80 | 186 | 8 | 26 | 81 | 46 |
| B12 - 0.25 mg/ml | 83 | 70 | 89 | 76 | 160 | 7 | 27 | 85 | 51 |
| AKG - 0.35 mg/ml | 86 | 73 | 95 | 82 | 170 | 7 | 27 | 85 | 50 |
| COMBO | 89 | 74 | 99 | 81 | 177 | 7 | 28 | 84 | 49 |

TABLE 16-continued

Combination AKG, Vitamin B12, and Combination (3 step)

|  | Motile | PROG | VAP | VSL | VCL | ALH | BCF | STR | LIN |
|---|---|---|---|---|---|---|---|---|---|
| Jersey 3 - 3 hr | | | | | | | | | |
| Control | 64 | 22 | 47 | 38 | 88 | 6 | 16 | 81 | 45 |
| B12 - 0.25 mg/ml | 73 | 52 | 64 | 52 | 104 | 10 | 20 | 81 | 51 |
| AKG - 0.35 mg/ml | 80 | 44 | 69 | 53 | 118 | 6 | 19 | 79 | 47 |
| COMBO | 77 | 30 | 56 | 44 | 107 | 7 | 19 | 79 | 42 |
| Jersey 3 - 6 hr | | | | | | | | | |
| Control | 16 | 0.5 | 38 | 24 | 54 | 1 | 17 | 64 | 47 |
| B12 - 0.25 mg/ml | 44 | 1 | 37 | 24 | 56 | 3 | 14 | 66 | 44 |
| AKG - 0.35 mg/ml | 79 | 11 | 46 | 33 | 84 | 6 | 15 | 74 | 41 |
| COMBO | 72 | 12 | 49 | 34 | 98 | 8 | 16 | 71 | 35 |

Example 17

In an additional experiment, motility and progressive motility of female and male sex-sorted Deer sperm were checked at 0, 1 and 3 hours after thawing the sex sorted semen samples that were treated with the antioxidant, vitamin B12 at two concentrations: 0.25 mg/ml and 0.35 mg/ml; all samples were treated during staining, catch and prior to cryopreservation (3 step). The OSR was not added to the control sample. The semen samples were derived from two white tailed bucks. Each sample was sorted for both male and female enriched populations of sperm.

TABLE 17

Deer (male and female) - Vitamin B12 (3 step)

| | | TOTAL | MOTILE | PROG | VAP | VSL | VCL | ALH | BCF | STR |
|---|---|---|---|---|---|---|---|---|---|---|
| | | 0 HR | | | | | | | | |
| | FEMALE | | | | | | | | | |
| Buck A | CONTROL | 1887 | 74 | 53 | 85 | 67 | 157 | 7 | 24 | 78 |
| | 0.25 | 2803 | 82 | 53 | 83 | 62 | 157 | 7 | 24 | 74 |
| | 0.35 | 2484 | 84 | 55 | 92 | 68 | 169 | 7 | 24 | 74 |
| | MALE | | | | | | | | | |
| | CONTROL | 2939 | 81 | 55 | 94 | 70 | 178 | 7 | 24 | 76 |
| | 0.25 | 3036 | 76 | 49 | 91 | 66 | 173 | 7 | 24 | 73 |
| | 0.35 | 2448 | 86 | 54 | 98 | 71 | 181 | 8 | 24 | 73 |
| | FEMALE | | | | | | | | | |
| Buck B | CONTROL | 2025 | 80 | 36 | 92 | 56 | 185 | 8 | 22 | 64 |
| | 0.25 | 1531 | 82 | 40 | 91 | 56 | 179 | 7 | 22 | 65 |
| | 0.35 | 1859 | 89 | 43 | 105 | 69 | 198 | 8 | 23 | 66 |
| | MALE | | | | | | | | | |
| | CONTROL | 2114 | 85 | 39 | 103 | 62 | 202 | 8 | 22 | 63 |
| | 0.25 | 1169 | 81 | 35 | 109 | 63 | 219 | 8 | 23 | 61 |
| | 0.35 | 1658 | 89 | 46 | 103 | 67 | 197 | 8 | 23 | 66 |
| | | 1 HR | | | | | | | | |
| | FEMALE | | | | | | | | | |
| Buck A | CONTROL | 1286 | 64 | 29 | 86 | 57 | 170 | 8 | 21 | 68 |
| | 0.25 | 1380 | 78 | 41 | 97 | 64 | 185 | 8 | 21 | 67 |
| | 0.35 | 1808 | 80 | 31 | 109 | 68 | 216 | 9 | 22 | 63 |
| | MALE | | | | | | | | | |
| | CONTROL | 1612 | 67 | 27 | 71 | 50 | 141 | 7 | 22 | 73 |
| | 0.25 | 1817 | 57 | 23 | 64 | 45 | 125 | 7 | 22 | 70 |
| | 0.35 | 3169 | 85 | 52 | 105 | 75 | 198 | 8 | 23 | 72 |
| | FEMALE | | | | | | | | | |
| Buck B | CONTROL | 1371 | 81 | 26 | 65 | 43 | 127 | 6 | 19 | 68 |
| | 0.25 | 1541 | 83 | 28 | 84 | 51 | 158 | 8 | 19 | 64 |
| | 0.35 | 2637 | 92 | 32 | 116 | 66 | 214 | 9 | 20 | 58 |

TABLE 17-continued

Deer (male and female) - Vitamin B12 (3 step)

|  |  | TOTAL | MOTILE | PROG | VAP | VSL | VCL | ALH | BCF | STR |
|---|---|---|---|---|---|---|---|---|---|---|
|  | MALE |  |  |  |  |  |  |  |  |  |
|  | CONTROL | 1520 | 84 | 48 | 86 | 57 | 169 | 6 | 23 | 70 |
|  | 0.25 | 1086 | 84 | 46 | 104 | 66 | 203 | 8 | 22 | 67 |
|  | 0.35 | 1881 | 92 | 46 | 112 | 71 | 216 | 8 | 22 | 65 |
|  |  |  |  | 2 HR |  |  |  |  |  |  |
|  | FEMALE |  |  |  |  |  |  |  |  |  |
| Buck A | CONTROL | 1188 | 58 | 16 | 58 | 42 | 114 | 7 | 18 | 74 |
|  | 0.25 | 1045 | 75 | 40 | 97 | 65 | 190 | 9 | 20 | 68 |
|  | 0.35 | 877 | 54 | 19 | 68 | 50 | 137 | 8 | 20 | 75 |
|  | MALE |  |  |  |  |  |  |  |  |  |
|  | CONTROL | 1325 | 59 | 13 | 51 | 38 | 101 | 6 | 19 | 77 |
|  | 0.25 | 1523 | 56 | 24 | 66 | 46 | 130 | 6 | 22 | 70 |
|  | 0.35 | 1797 | 58 | 39 | 101 | 75 | 193 | 8 | 23 | 76 |
|  | FEMALE |  |  |  |  |  |  |  |  |  |
| Buck B | CONTROL | 1125 | 73 | 15 | 56 | 38 | 111 | 7 | 18 | 69 |
|  | 0.25 | 834 | 64 | 11 | 53 | 36 | 106 | 7 | 16 | 68 |
|  | 0.35 | 1378 | 85 | 26 | 100 | 57 | 190 | 8 | 19 | 60 |
|  | MALE |  |  |  |  |  |  |  |  |  |
|  | CONTROL | 1603 | 77 | 37 | 66 | 46 | 126 | 6 | 19 | 73 |
|  | 0.25 | 866 | 78 | 47 | 95 | 67 | 111 | 7 | 21 | 71 |
|  | 0.35 | 1760 | 89 | 41 | 78 | 51 | 149 | 7 | 20 | 70 |

As can be easily understood from the foregoing, the basic concepts of the present invention may be embodied in a variety of ways. As such, the particular embodiments, elements, terms, or expressions disclosed by the description, or shown in the figures accompanying this application are not intended to be limiting, but rather are examples of the numerous and varied embodiments generically encompassed by the invention or its equivalents with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As example, it should be understood that all steps of a method may be disclosed as an action, a means for taking that action, or as an element which causes that action. Similarly, each element of an apparatus may be disclosed as the physical element or the action which that physical element facilitates. As another example, the disclosure of a "sorter" should be understood to encompass disclosure of the act of "sorting," whether explicitly discussed or not, and conversely, effective disclosure of the act of "sorting" should be understood to encompass disclosure of a "sorter." Such alternative terms for each element or step are to be understood to be explicitly included in the description.

In addition, it should be understood that unless utilization of a specific term in this application is inconsistent with common use and interpretation of that term, dictionary definitions should be understood to be included in the description for each term as contained in the Random House Webster's Unabridged Dictionary, second edition, each definition hereby incorporated by reference.

Moreover, for the purposes of the present invention, the term "a" or "an" before an item also refers to one or more of that item; for example, "a container" refers to one or more of the containers. As such, the terms "a" or "an", "one or more" and "at least one" can be used interchangeably herein. Further, as used herein the term "or" means "and/or" unless specifically indicated otherwise.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the present invention, and the terms used in those earlier documents which may be similarly used in this disclosure, shall not alter the intended definition of those same terms as defined or intended herein.

The claims set forth in this specification, if any, are hereby incorporated by reference as part of the description of the current invention, and the applicant expressly reserves the right to use all or a portion of such incorporated content as additional description to support any or all of the claims or any element or component thereof. The applicant further expressly reserves the right to move any portion or all of the incorporated content of such claims or any element or component thereof from the description into the claims, or vice versa, as necessary to define the invention for which protection is sought by this application or by any subsequent application or continuation, division, or continuation-in-part application thereof, or to obtain any benefit for reduction in fees in compliance with relevant patent laws, rules, or regulations of any country or treaty, and such incorporate content shall survive the entire pendency of this application as well as any subsequent continuation, division, continuation-in-part application filings or any reissue or extension thereof.

The claims set forth in this specification are intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

The invention claimed is:

1. A method of fertilizing one or more eggs, comprising the steps of:
   providing a sperm cell sample in a media making a sperm cell composition, wherein the media comprises vitamin B12, or a vitamin B12 vitamer, at a concentration of about 0.01 mg/ml to 1 mg/ml and alpha-ketoglutarate; and
   contacting the one or more eggs with one or more sperm cells from the sperm cell composition.

2. The method of claim 1, wherein the concentration of the vitamin B12, or the vitamin B12 vitamer, in the media is selected from the group consisting of: 0.01 to 0.25 mg/ml; 0.01 to 0.5 mg/ml; 0.05 to 0.1 mg/ml; 0.05 to 1.0 mg/ml; 0.1 to 0.25 mg/ml; 0.1 to 0.5 mg/ml; 0.1 to 1 mg/ml; 0.15 to 0.45 mg/ml; 0.15 to 0.5 mg/ml; 0.25 to 0.35 mg/ml; 0.25 to 0.5 mg/ml; 0.25 to 1 mg/ml; 0.35 to 0.5 mg/ml; 0.35 to 1 mg/ml; and 0.5 to 1 mg/ml.

3. The method of claim 1, wherein the concentration of the vitamin B12, or the vitamin B12 vitamer, in the media is selected from the group consisting of: about 0.05 mg/ml; about 0.1 mg/ml; about 0.15 mg/ml; about 0.25 mg/ml; about 0.35 mg/ml; about 0.45 mg/ml; and about 0.5 mg/ml.

4. The method of claim 1, wherein the concentration of the vitamin B12, or the vitamin B12 vitamer, in the media is about 0.15 mg/ml, about 0.25 mg/ml or about 0.35 mg/ml.

5. The method of claim 1, wherein the concentration of the vitamin B12, or the vitamin B12 vitamer, in the media is about 0.25 mg/ml.

6. The method of claim 1, wherein the concentration of the alpha-ketoglutarate in the media is about 0.15 mg/ml to 0.5 mg/ml.

7. The method of claim 1, wherein the sperm cell sample has been sex-sorted.

8. The method of claim 1, wherein the sperm cell sample has been processed by ablating unwanted cells.

9. The method of claim 1, further comprising the step of freezing and thawing the sperm cell sample or the sperm cell composition.

10. The method of claim 1, wherein the sperm cell sample is derived from a human, bovine, swine, ovine, equine, deer, elk, buffalo, canine, feline, chimpanzee or gorilla, or a whale, dolphin or other marine mammal.

11. A method of fertilizing one or more eggs, comprising the steps of:
    providing a sex-sorted sperm cell sample, or a sperm cell sample processed by ablating unwanted cells, in a media making a sperm cell composition, wherein the media comprises vitamin B12, or a vitamin B12 vitamer, at a concentration of about 0.01 mg/ml to 1 mg/ml; and
    contacting the one or more eggs with one or more sperm cells from the sperm cell composition.

12. The method of claim 11, wherein the concentration of the vitamin B12, or the vitamin B12 vitamer, in the media is about 0.15 mg/ml, about 0.25 mg/ml or about 0.35 mg/ml.

13. The method of claim 11, wherein the concentration of the vitamin B12, or the vitamin B12 vitamer, in the media is about 0.25 mg/ml.

14. The method of claim 11, wherein the media further comprises alpha-ketoglutarate.

15. The method of claim 11, further comprising the step of freezing and thawing the sperm cell sample or the sperm cell composition.

16. The method of claim 11, wherein the sperm cell sample is derived from a human, bovine, swine, ovine, equine, deer, elk, buffalo, canine, feline, chimpanzee or gorilla, or a whale, dolphin or other marine mammal.

* * * * *